US007332523B2

(12) United States Patent
Satchi-Fainaro et al.

(10) Patent No.: US 7,332,523 B2
(45) Date of Patent: Feb. 19, 2008

(54) TNP-470 POLYMER CONJUGATES AND USE THEREOF

(75) Inventors: Ronit Satchi-Fainaro, Chestnut Hill, MA (US); Judah Folkman, Brookline, MA (US)

(73) Assignee: Children's Medical Center Corporation, Boston, MA (US)

( * ) Notice: Subject to any disclaimer, the term of this patent is extended or adjusted under 35 U.S.C. 154(b) by 74 days.

(21) Appl. No.: 10/511,009

(22) PCT Filed: Apr. 10, 2003

(86) PCT No.: PCT/US03/10976

§ 371 (c)(1),
(2), (4) Date: Mar. 24, 2005

(87) PCT Pub. No.: WO03/086382

PCT Pub. Date: Oct. 23, 2003

(65) Prior Publication Data

US 2005/0169881 A1    Aug. 4, 2005

Related U.S. Application Data

(60) Provisional application No. 60/371,791, filed on Apr. 11, 2002, provisional application No. 60/414,705, filed on Sep. 30, 2002.

(51) Int. Cl.
*A61K 31/336* (2006.01)
*A61K 38/04* (2006.01)
*A61P 9/00* (2006.01)
*A61P 35/04* (2006.01)
*C07D 407/08* (2006.01)

(52) U.S. Cl. ..................... 514/475; 549/332
(58) Field of Classification Search ............... 514/475; 549/332
See application file for complete search history.

(56) References Cited

U.S. PATENT DOCUMENTS

| 5,037,883 A | 8/1991 | Kopecek et al. |
| 5,164,410 A | 11/1992 | Kishimoto et al. |
| 5,166,172 A | 11/1992 | Kishimoto et al. |
| 5,180,735 A | 1/1993 | Kishimoto et al. |
| 5,180,738 A | 1/1993 | Kishimoto et al. |
| 5,290,807 A | 3/1994 | Folkman et al. |
| 5,698,586 A | 12/1997 | Kishimoto et al. |
| 6,017,954 A | 1/2000 | Folkman et al. |
| 6,022,888 A | 2/2000 | Morishige et al. |
| 6,225,478 B1 | 5/2001 | Morishige et al. |

FOREIGN PATENT DOCUMENTS

| WO | WO 01/36002 | 5/2001 |
| WO | WO 01/97776 | 12/2001 |
| WO | WO 02/098446 | 12/2002 |
| WO | WO 03/086178 A | 10/2003 |

OTHER PUBLICATIONS

Folkman, J., Angiogenesis. in *Harrison's Textbook of Internal Medicine* (eds. Braunwald, E. et al.) 517-530 (McGraw Hill, New York, 2001).
Hanahan, D. et al., Patterns and emerging mechanisms of the angiogenic switch during tumorigenesis, *Cell*, 86:353-64 (1996).
Volpert, O.V. et al., Id1 regulates angiogenesis through transcriptional repression of thrombospondin-1, *Cancer Cell*, 2:473-483 (2002).
Folkman, J., Tumor angiogenesis, *Cancer Medicine* (eds. Holland, J., et al.) pp. 132-152 (B. C. Decker Inc., Ontario, Canada, 2000).
Lyden, D. et al., Id1 and Id3 are required for neurogenesis, angiogenesis and vascularization of tumour xenografts, *Nature*, 401:670-677 (1999).
Streit, M. et al.; Thrombospondin-2: a potent endogenous inhibitor of tumor growth and angiogenesis, *Proc. Natl. Acad. Sci. USA*, 96:14888-14893 (1999).
Chin, L. et al., Essential role for oncogenic Ras in tumour maintenance, *Nature*, 400:468-472 (1999).
Tabone, M.D. et al., Are basic fibroblast growth factor and vascular endothelial growth factor prognostic indicators in pediatric patients with malignant solid tumors?, *Clinical Cancer Res.*, 7:538-543 (2001).
Yao, Y. et al., Prognostic value of vascular endothelial growth factor and its receptors Flt-1 and Flk-1 in astrocyctic tumours, *Acta Neurochir (Wien)*, 143:159-66 (2001).
Yuan, A. et al., Aberrant p53 expression correlates with expression of vascular endothelial growth factor mRNA and interleukin-8 mRNA and neoangiogenesis in non-small-cell lung cancer, *J. Clinical Oncology*, 20:900-910 (2002).
Ingber, D. et al., Synthetic analogues of fumagillin that inhibit angiogenesis and suppress tumour growth, *Nature*, 348:555-557 (1990).
Antoine, N. et al., AGM-1470, a potent angiogenesis inhibitor, prevents the entry of normal but not transformed endothelial cells into the $G_1$ phase of the cell cycle, *Cancer Res.*, 54:2073-2076 (1994).
Kudelka, A.P. et al., Complete remission of metastic cervical cancer with the angiogenesis inhibitor TNP-470, *N. Engl. J. Med.*, 338:991-2 (1998).
Kudelka, A.P. et al., A phase I study of TNP-470 administered to patients with advanced squamous cell cancer of the cervix, *Clinical Cancer Res.*, 3:1501-1505 (1997).
Bhargava, P. et al., A Phase I and pharmacokinetic study of TNP-470 administered weekly to patients with advanced cancer, *Clinical Cancer Res.*, 5:1989-1995 (1999).

(Continued)

*Primary Examiner*—Venkataraman Balasubramanian
(74) *Attorney, Agent, or Firm*—Nixon Peabody LLP

(57) ABSTRACT

The present invention relates to conjugates of water-soluble polymers and o(chloracetyl-carbamoyl) fumagillol (TNP-470) and use of those conjugates as specific intracellular carriers of the TNP-470 into tumor vessels. The present invention further relates to use of those conjugates to lower the neurotoxicity of TNP-470. Preferably, the polymer has a molecular weight in the range of 100 Da to 800 kDa. More preferably, the polymer has a molecular weight no greater than 60 kDa. Most preferably, the polymer has a molecular weight in the range of 15 kDa to 40 kDa.

13 Claims, 13 Drawing Sheets

OTHER PUBLICATIONS

Herbst, R.S. et al., Safety and pharmacokinetic effects of TNP-470, an angiogenesis inhibitor, combined with paclitaxel in patients with solid tumors: evidence for activity in non-small-cell lung cancer, *J. Clinical Oncol.*, 20:4440-4447 (2002).

Kim, E.S. et al., Angiogenesis inhibitors in lung cancer. *Curr. Oncol. Rep.*, 4:325-333 (2002).

Stadler, W.M. et al., Multi-institutional study of the angiogenesis inhibitor TNP-470 in metastatic renal carcinoma, *J. Clinical Oncol.*, 17:2541-2545 (1999).

Logothetis, C.J. et al., Phase I trial of the angiogenesis inhibitor TNP-470 for progressive androgen-independent prostate cancer. *Clinical Cancer Res.*, 7:1198-1203 (2001).

Rupnick, M.A. et al., Adipose tissue mass can be regulated through the vasculature, *Proc. Natl. Acad. Sci. U S A*, 99:10730-10735 (2002).

Schoof, D.D. et al., The influence of angiogenesis inhibitor AGM-1470 on immune system status and tumor growth in vitro, *Int. J. Cancer*, 55:630-635 (1993).

Nagabuchi, E. et al., TNP-470 antiangiogenic therapy for advanced murine neuroblastoma, *J. Pediatric Surg.*, 32:287-93 (1997).

Rihova, B. et al., Biocompatibility of N-(2-hydroxypropyl) methacrylamide copolymers containing adriamycin. Immunogenicity, and effect on haematopoietic stem cells in bone marrow in vivo and mouse splenocytes and human peripheral blood lymphocytes in vitro, *Biomaterials*, 10:335-342. (1989).

Seymour, L.W. et al., The pharmacokinetics of polymer-bound adriamycin, *Biochem. Pharmacol.*, 39:1125-1131 (1990).

Maeda, H. et al., Tumor vascular permeability and the EPR effect in macromolecular therapeutics: a review, *J. Controlled Release*, 65:271-284 (2000).

Duncan, R. et al., Preclinical toxicology of a novel polymeric antitumour agent: HPMA copolymer-doxorubicin (PK1), *Human and Exp. Toxicology*, 17:93-104 (1998).

Satchi-Fainaro, R., Targeting tumor vasculature: Reality or a dream?.*J. Drug Targeting*, 10:529-533 (2002).

Duncan, R. et al., Polymers containing enzymatically degradable bonds, 7. Design of oligopeptide side chains in poly [N-(2-hydroxypropyl)methacrylamide] copolymers to promote efficient degradation by lysosomal enzymes, *Makromol. Chem.*, 184:1997-2008 (1983).

Foekens, J.A. et al., Prognostic significance of cathepsins B and L in primary human breast cancer. *J. Clinical Oncol.*, 16:1013-1021 (1998).

Gianasi, E. et al.. HPMA copolymer platinates as novel antitumour agents: in vitro properties, pharamcokinetics and antitumour activity in vivo, *Eur. J. Cancer*, 35:994:1002.

Kusaka, M. et al. Cytostatic inhibition of endothelial cell growth by the angiogenesis inhibitor TNP-470 (AGM-1470), *Br. J. Cancer.* 69:212-216 (1994).

Greene, A.K. et al., Endothelial-directed hepatic regeneration after partial hepatectomy, *Ann. Surg.*, 237:530-535 (2003).

Drixler, T.A. et al., Liver regeneration is an angiogenesis-associated phenomenon, *Ann. Surg.*, 236:703-712 (2002).

Klein, S.A. et al., Angiogenesis inhibitor TNP-470 inhibits murine cutaneous wound healing, *J. Surg. Res.*, 82:268-274 (1999).

Whalen, C.T. et al., Assay of TNP-470 and its two major metabolites in human plasma by high-performance liquid chromatography-mass spectrometry, *J. Chromatorgraphic Sci.*, 40:214-218 (2002).

Brocchini, S. et al., Polymer-Drug conjugates: drug release from pendent linkers. in *Encyclopaedia of controlled release* (ed. Mathiovitz, E.) 786-816 (New York: Wiley, 1999).

Duncan, R. et al., Polymer-drug conjugates, PDEPT and PELT: basic principles for design and transfer from the laboratory to clinic, *J. Controlled Release*, 74:135-146 (2001).

Vasey, P.A. et al., Phase 1 clinical and pharmacokinetic study of PK1 [N-(2-hydroxypropyl)methacrylamide copolymer doxorubicin]: first member of a new class of chermotherapeutic agents-drug-polymer conjugates, Cancer Research Campaign Phase I/II Committee, *Clinical Cancer Res.*, 5:83-94 (1999).

Seymour, L.W. et al., Tumour tropism and anti-cancer efficacy of polymer-based doxorubicin prodrugs in the treatment of subcutaneous murine B16F10 melanoma, *Br. J. Cancer*, 70:636-641 (1994).

Dvorak, H.F. et al., Identification and characterization of the blood vessels of solid tumors that are leaky to circulating macromolecules. *Am. J. Pathology*. 133:95-109 (1988).

Griffith, E.C. et al., Methionine aminopeptidase (type 2) is the common target for angiogenesis inhibitors AGM-1470 and ovalicin, *Chem. and Biol.*, 4, 461-471 (1997).

Auerbach, R. et al., Angiogenesis assays: problems and pitfalls, *Cancer Metastasis Rev.*, 19:167-172 (2000).

Seymour, L.W. et al., Hepatic drug targeting: phase I evaluation of polymer-bound dioxorubicin., *J. Clinical Oncol.*, 20:1668-1676 (2002).

Francis, G.E. et al., PEG-modified proteins. in *Stability of Proteins Pharmaceuticals (Part B)* (ed. Ahem TJ, M.M.) 235-263 (Plenum Press, New York, 1992).

Ho, D.H. et al:, Clinical pharmacology of polyethylene glycol-L-asparaginase, *Drug Metabolism Disposition*, 14:349-352 (1986).

O'Reilly, M.S. et al., Angiostatin: a novel angiogenesis inhibitor that mediates the suppression of metastases by a Lewis lung carcinoma, *Cell*, 79:315-328 (1994).

Folkman, J. et al., Long-term culture of capillary endothelial cells, *Proc. Natl. Acad. Sci. USA*, 76:5217-5221 (1979).

Waynforth, H.B. Routes and methods of administration, Intracerebral injection. in *Experimental and Surgical technique in the rat*, vol. 2.9 34-36 (Academic Press, London, 1980).

Seymour, L.W. et al., The pharmacokinetics of polymer-bound adriamycin, *Biochemical Pharmacology*, 39:1125-1131 (1990).

Yeh, J.R. et al., The antiangiogenic agent TNP-470 requires p53 and $p21^{CIP/WAF}$ for endothelial cell growth arrest, *Proc. Natl. Acad. Sci. USA*, 97:12782-12787 (2000).

Zhang, Y. et al., Cell cycle inhibition by the anti-angiogenic agent TNP-470 is mediated by p53 and $p21^{WAF/CIP1}$, *Proc. Natl. Acad. Sci. USA*, 97:6427-6432 (2000).

Seymour, L. W. et al., N-(2-hydroxypropyl) methacrylamide copolymers targeted to the hepatocyte galatose-receptor: pharmacokinetics in $DBA_2$ mice, *Br. J. Cancer*, 63:859-866 (1991).

Folkman, J. Tumor angiogenesis. in *Accomplishments in cancer research* (eds. Wells, S.J. & Sharp, P.) 32-44 (Lippincott Williams & Wilkins, New York, 1998).

Noguchi, A., et al., *Bioconjugate Chem.*, 3 (2): 132-137 (1992).

Yasukawa, T., et al., *IOVS 40* (11): 2690-2696 (1999).

Yamaoka, T., et al, *Journal of Pharmaceutical Sciences*, 83 (4): 601-606 (1994).

Yamaoka, T., et al., *Journal of Pharmaceutical Pharmacology*, 47: 479-486 (1995).

Murakami, Y., et al., *Drug Delivery*, 4: 23-31 (1997).

Satchi, R. et al., *British J. of Cancer*, 85(7):1070-1076 (2001).

Murakami, Y., et al., *Drug Delivery*. 4:23-31 (1997). Tumor Accumulation of Poly(Ethylene Glycol) with Different Molecular Weights After Intravenous Injection.

TNP-470 POLYMER CONJUGATES AND USE THEREOF

CROSS-REFERENCE TO RELATED APPLICATIONS

This application is a 371 National Stage of International Application No. PCT/US03/10976 filed on Apr. 10, 2003, which designated the U.S., and which claims the benefit under 35 U.S.C. § 119(e) of U.S. Provisional Application Nos. 60/371,791 filed on Apr. 11, 2002 and 60/414,705 filed on Sep. 30, 2002.

BACKGROUND OF THE INVENTION

In recent years, it has become clear that angiogenesis, the growth of new capillary blood vessels from pre-existing vasculature, is important not only in physiological processes such as embryonic development, the female reproductive cycle, wound healing, and organ and tissue regeneration, but also in pathological processes such as tumor progression and metastasis[1]. Angiogenesis is now recognized as a critical process for all malignancies[2,3]. As a result, the microvascular endothelial cell, which is recruited by tumors, has become an important second target in cancer therapy. It is widely accepted that the endothelial cell target, unlike the tumor cells themselves, is genetically stable[1]. Antiangiogenic agents have recently emerged as a new class of drugs; however, the optimal means to use these agents alone or in combination with drug delivery systems and with conventional chemotherapy have not yet been fully elucidated.

The hypothesis that tumor growth is angiogenesis-dependent is supported by biological and pharmacological evidence[4] and confirmed by genetic evidence[3,5-7]. Both types of evidence provide a scientific basis for current clinical trials of angiogenesis inhibitors. Increased tumor angiogenesis[4,8] and elevated levels of proangiogenic factors such as vascular endothelial growth factor (VEGF/VPF)[8,9], basic fibroblast growth factor (bFGF)[8], and interleukin-8 (IL-8)[10] correlate with decreased survival and increased risk of relapse in studies of patients with malignant solid tumors. The importance of angiogenesis is further supported by the observation that antiangiogenic agents inhibit tumor growth in a variety of animal models.

In the U.S. there are currently more than 30 angiogenesis inhibitors in various clinical trials for late-stage cancer. One of these angiogenesis inhibitors, O-(chloracetyl-carbamoyl) fumagillol (TNP-470), is a low molecular weight synthetic analogue of fumagillin[11], a compound secreted by the fungus *Aspergillus fumigatus* fresenius. TNP-470 is a potent endothelial inhibitor in vitro[12]. Recently, TNP-470 has been tested as a potential new anticancer agent. In animal models, TNP-470 has the broadest anticancer spectrum of any known agent[4,13]. TNP-470 inhibited the growth of murine tumors up to 91%, human tumors up to 100% and metastatic tumors up to 100% in mice (reviewed in ref. [13]). In most studies, mice were treated at the same optimal dose of 30 mg/kg subcutaneously every other day. In clinical trials TNP-470 has shown evidence of antitumor activity when used as a single agent, with a number of objective responses reported with relapsed and refractory malignancies[14-16]. It has also shown promise when used in combination with conventional chemotherapy[17,18]. However, many patients experience neurotoxicity (malaise, rare seizures, asthenia, anxiety and dysphoria)[16,17,19,20] at doses where antitumor activity has been seen. Because of dose-limiting neurotoxicity, TNP-470 has been tested using multiple dosing regimens, but these attempts to limit its toxicity have been unsuccessful. With few exceptions, weight loss or failure to gain weight was observed in animals receiving TNP-470[21], and two reports noted a decrease in splenic weight[22,23]. Therefore, modifications of TNP-470 that can retain or increase its activity while reducing its toxicity are highly desirable.

SUMMARY OF THE INVENTION

The present invention relates to conjugates of water-soluble polymers and o-(chloracetyl-carbamoyl) fumagillol (TNP-470) and use of those conjugates as specific intracellular carriers of the TNP-470 into tumor vessels. The present invention further relates to use of those conjugates to lower the neurotoxicity of TNP-470. Preferably, the polymer has a molecular weight in the range of 100 Da to 800 kDa. More preferably, the polymer has a molecular weight no greater than 60 kDa. Most preferably, the polymer has a molecular weight in the range of 15 kDa to 40 kDa.

Preferred polymers are HPMA copolymers. HPMA copolymers are biocompatible, non-immunogenic and non-toxic carriers that enable specific delivery into tumor endothelial cells overcoming limitations of drug-related toxicities (Duncan, et al., *Hum Exp Toxicol*, 17:93-104 (1998)). Moreover, their body distribution is well characterized and they are known to accumulate selectively in the tumor site due to the enhanced permeability and retention (EPR) effect (Maeda, et al., *J Controlled Release*, 65:271-284 (2000)). The conjugate can also include a targeting moiety to direct the conjugate to sites of endothelial cell proliferation or cancer cells or to specific receptors or markers associated with proliferating endothelial cells.

The data presented herein demonstrate that TNP-470 conjugated to an HPMA copolymer: (i) avoid high peak drug levels in the circulation (ii) avoid penetration of TNP-470 to the cerebrospinal fluid and thus prevent the problem of neurotoxicity; (iii) prolong its half-life; (iv) facilitate the accumulation of TNP-470 in tissues involving neovascularization; (v) convert TNP-470 to a highly effective and widely useful angiogenesis inhibitor. We have also surprisingly discovered that conjugating TNP-470 to HPMA results in a water soluble composition.

The present invention further relates to use of the conjugates in methods of treating angiogenic diseases and decreasing neurotoxicity of TNP-470. Angiogenic disease amenable to treatment with the present invention include but are not limited to diabetic retinopathy, macular degeneration, retrolental fibroplasia, trachoma, neovascular glaucoma, psoriases, angio-fibromas, immune and non-immune inflammation, capillary formation within atherosclerotic plaques, hemangiomas, excessive wound repair, solid tumors, metastases, Kaposi's sarcoma and the like.

In accordance with the present invention, if polymer a having a molecular weight greater than 60 kDa is used, it is preferred that the polymer be a degradable polymer or inert.

As used herein, a "degradable" polymer is one that breaks down in vivo to components having a molecular weight no greater than 60 kD. As defined herein, poly vinyl alcohol (PVA) is not a degradable polymer.

Other aspects of the invention are disclosed infra.

BRIEF DESCRIPTION OF THE DRAWINGS

FIG. 4 shows antitumour activity measured using male SCID mice bearing A2058 human melanoma.

FIG. 5 shows antitumour activity measured using male C57 mice bearing LLC.

DETAILED DESCRIPTION OF THE INVENTION

Figure 1A:
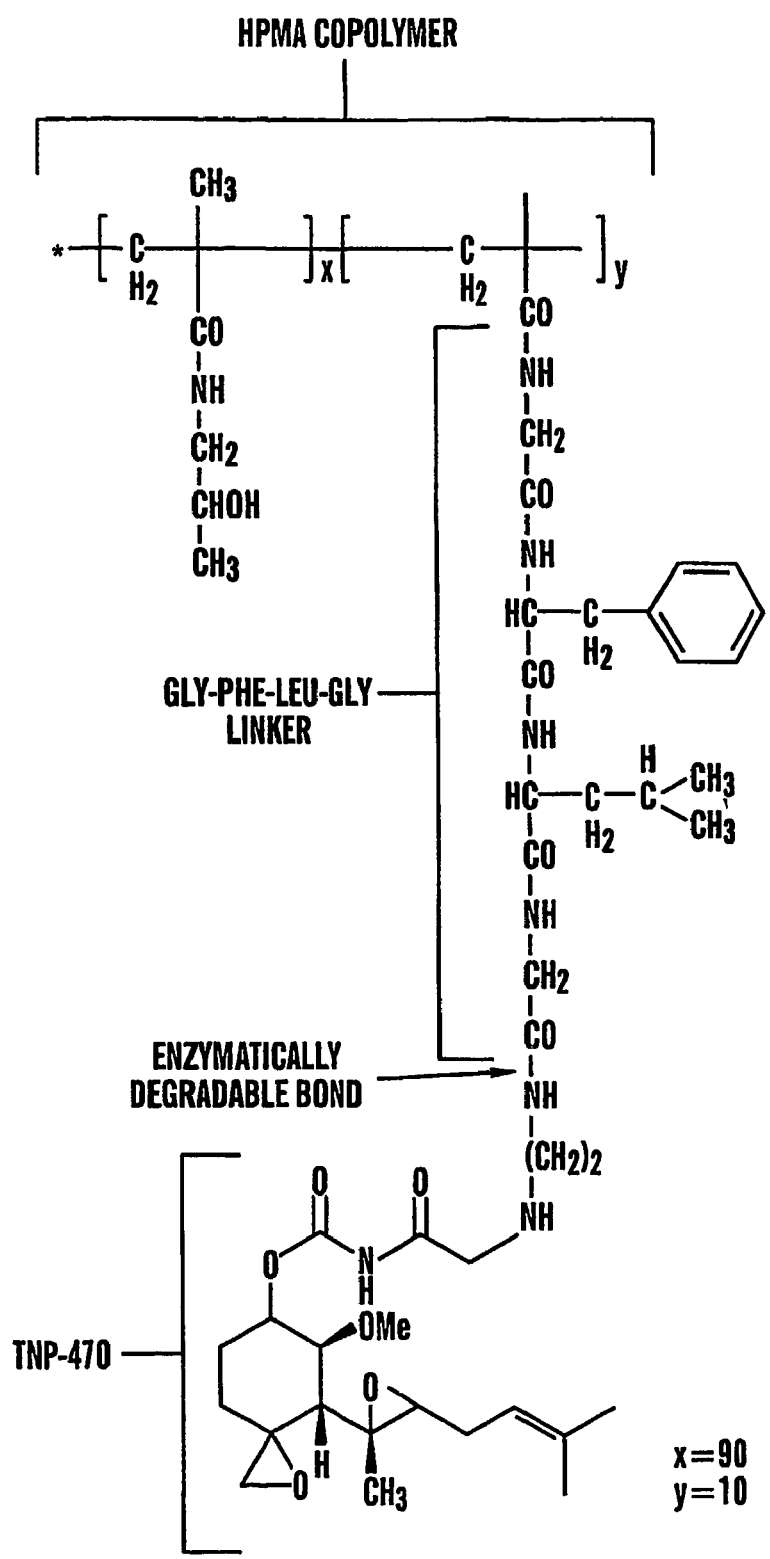
FIG. 1A illustrates the structure of HPMA copolymer-Gly-Phe-Leu-Gly-ethylenediamine-TNP-470.

The present invention relates to polymer and copolymer conjugates of TNP-470.

In accordance with the present invention, the TNP-470 is linked to a water soluble degradable or non-degradable polymer having a molecular weight in the range of 100 Da to 800 kDa. The components of the polymeric backbone may comprise acrylic polymers, alkene polymers, urethane-polymers, amide polymers, polyimines, polysaccharides and ester polymers. Preferably the polymer is synthetic rather than being a natural polymer or derivative thereof. Preferably the backbone components comprise derivatised polyethyleneglycol and poly(hydroxyalkyl(alk)acrylamide), most preferably amine derivatised polyethyleneglycol or hydroxypropyl(meth)acrylamide-methacrylic acid copolymer or derivative thereof. Dextran/dextrin and polyethylene glycol polymers, or derivatives thereof, may also be used. Preferably, the polymer has a molecular weight no greater than 60 kDa. A most preferred molecular weight range is 15 to 40 kDa.

The TNP-470 and the polymer are conjugated by use of a linker, preferably a cleavable peptide linkage. Most preferably, the peptide linkage is capable of being cleaved by preselected cellular enzymes, for instance, those found in lysosomes of cancerous cells or proliferating endothelial cells. Alternatively, an acid hydrolysable linker could comprise an ester or amide linkage and be for instance, a cis-aconityl linkage. A pH sensitive linker may also be used.

Cleavage of the linker of the conjugate results in release of active TNP-470. Thus the TNP-470 must be conjugated with the polymer in a way that does not alter the activity of the agent. The linker preferably comprises at least one cleavable peptide bond. Preferably the linker is an enzyme cleavable oligopeptide group preferably comprising sufficient amino acid units to allow specific binding and cleavage by a selected cellular enzyme. Preferably the linker is at least two amino acids long, more preferably at least three amino acids long.

Preferred polymers for use with the present invention are HPMA copolymers with methacrylic acid with pendent oligopeptide groups joined via peptide bonds to the methacrylic acid with activated carboxylic terminal groups such as paranitrophenyl derivatives or ethylene diamine.

In a preferred embodiment the polymeric backbone comprises a hydroxyalkyl(alk)acrylamide methacrylamide copolymer, most preferably a copolymer of hydroxypropyl (meth)acrylamide copolymer (HPMA). The HPMA prior to attachment of the TNP-470 has the structure set forth below:

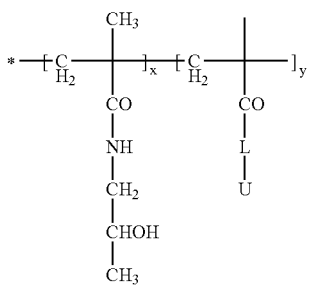

y can be in the range of 0.01-100 and x can be in the range 0-99.99. y is preferably in the range of 0.04-20 and x is preferably in the range 80-99.96. Preferably L is an oligopeptide group containing between 2 and 10 peptide moieties, most preferably 3 or 4.

In a most preferred embodiment, L is a Gly-Phe-Leu-Gly-linkage. In one embodiment, U is an ONp group, wherein Np is a p-nitrophenyl group. Preferably y is in the range 0.3 to 15 and x is in the range of 99.7 to 85. Most preferably, y is in the range of 5-10 and x is in the range of 90-95. In a more preferred embodiment, the polymeric backbone is HPMA copolymer-Gly-Phe-Leu-Gly-ethylenediamine having the values for x and y as defined above.

In a most preferred embodiment of HPMA copolymer TNP-470 conjugate has the structure set forth in FIG. 1A.

HPMA polymers and use thereof are disclosed in WO 01/36002.

In another embodiment, the conjugate is a liposome/TNP-470 conjugate. Preferably, the conjugate is a pegylated liposomal TNP-470. An exemplary conjugate comprises:
a) TNP-470;
b) N-(carbonyl-methoxypolyethylene glycol 2000)-1,2-distearoyl-sn-glycero-3-phosphoethanolamine sodium salt;
c) fully hydrogenated soy phosphatidylcholine;
d) cholesterol;

Histidine, hydrochloric acid and/or sodium hydroxide, ammonium sulfate, and sucrose; wherein the weight percentage ratio of a:b:c:d is about 1.0:1.60:4.80:1.60 mg/mL respectively.

While the antiangiogenic agent conjugate may rely for its localization at a solid tumor, or other sites of active angiogenesis, primarily upon EPR, it may be desirable to attach ligands allowing active targeting. A preferred targeting ligand is directed to the integrin α Vβ3 and contains the tripeptide sequence RGD. Antibodies or ligands directed to cell receptors or other upregulated molecules present on the cell surface may also be used. See, e.g. 28.

The conjugate of the present invention is useful in inhibiting the angiogenic function of endothelial cells both in vitro and in vivo. Of particular interest is the prevention or inhibition of endothelial cell differentiation into capillary structures. The endothelial cells amenable to inhibition by the conjugate are present at several sites in a mammal and include but are not limited to dermis, epidermis, endometrium, retina, surgical sites, gastrointestinal tract, liver, kidney, reproductive system, skin, bone, muscle, endocrine system, brain, lymphoid system, central nervous system, respiratory system, umbilical cord, breast tissue, urinary tract and the like. The method of treatment of the present invention using the conjugate is particularly useful in preventing or inhibiting angiogenesis by endothelial cells at sites of inflammation and tumorigenesis.

The conjugate is particularly useful in methods of inhibiting angiogenesis at a site of tumorigenesis in a mammal. The conjugate administered at such sites prevents or inhibits blood vessel formation at the site thereby inhibiting the development and growth of the tumor. Tumors which may be prevented or inhibited by preventing or inhibiting angiogenesis with the conjugate include but are not limited to melanoma, metastases, adenocarcinoma, sarcomas, thymoma, lymphoma, lung tumors, liver tumors, colon tumors, kidney tumors, non-Hodgkins lymphoma, Hodgkins lymphoma, leukemias, uterine tumors, breast tumors, prostate tumors, renal tumors, ovarian tumors, pancreatic tumors, brain tumors, testicular tumors, bone tumors, muscle tumors, tumors of the placenta, gastric tumors and the like.

In providing a mammal with the conjugate, preferably a human, the dosage of administered conjugate will vary depending upon such factors as the mammal's age, weight, height, sex, general medical condition, previous medical history, disease progression, tumor burden, route of administration, formulation and the like. For example, a suitable dose of the conjugate for a mammal in need of treatment as described herin is in the range of about 1 mg to about 2000 mg TNP-470 per kilogram of body weight.

The route of administration may be intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor and the like.

The present invention encompasses combination therapy in which the conjugate is used in combination with a chemotherapeutic agent such as Taxol, cyclophosphamide, cisplatin, gancyclovir and the like. The chemotherapeutic agent may also be conjugated to a polymer. Such a therapy is particularly useful in situations in which the mammal to be treated has a large preexisting tumor mass which is well vascularized. The chemotherapeutic agent serves to reduce the tumor mass and the conjugate prevents or inhibits neovascularization within or surrounding the tumor mass. The chemotherapeutic agent may also be administered at lower doses than normally used and at such doses may act as an antiangiogenic agent.

The present invention is further illustrated by the following Examples. These examples are provided to aid in the understanding of the invention and are not construed as a limitation thereof.

EXAMPLE 1

Methods

Materials

A random copolymer of HPMA copolymerized with methacryloyl-Gly-Phe-Leu-Gly-p-nitrophenyl ester (HPMA copolymer-MA-GFLG-ONp) incorporating approximately 10 mol % of the MA-GFLG-ONp monomer units was prepared as previously reported[24] and provided by Polymer Laboratories (UK). The polymeric precursor was used for ethylenediamine (en) incorporation and the product HPMA copolymer-GFLG-en had a Mw of 31,600 Da and polydispersity (PD) of 1.66. TNP-470 was kindly provided by Douglas Figg from the NCI (USA). 2-Propanol, methanol, orthophosphoric acid and chloroform were from Sigma (all HPLC grade). Dimethylformamide (DMF) and dimethylsulfoxide (DMSO) were from Aldrich (ISA). All other chemicals were of analytical grade from Aldrich (USA) and Fisher Chemicals (USA) unless otherwise stated. Vivacell 70 ml (10 kDa MW cut-off PES) was from VivaScience (USA). Isoflurane was purchased from Baxter Healthcare Corporation (USA). Matrigel basement membrane matrix (from Engelbreth-Holm-Swarm mouse tumor) was purchased from Becton Dickinson (USA). Avertin was purchased from Fisher (USA).

A2058 human melanoma cells were from the ATCC. LLC cells were passaged from mouse to mouse as previously described[47]. Cells were maintained in DMEM medium containing 10% inactivated fetal bovine serum (Life Technologies, Inc.), 0.29 mg/ml L-glutamine, 100 units/ml penicillin and 100 µg/ml streptomycin (GPS) (Gibco) in a humidified 5% $CO_2$ incubator at 37° C. BCE cells were isolated in our laboratory, and cultured in a humidified 10% $CO_2$ incubator at 37° C. as described[48]. BCE cells were grown in DMEM medium supplemented with 10% bovine calf serum (BCS), GPS, and 3 ng/ml basic fibroblast growth factor (bFGF). C57BL/6J mice were purchased from Jackson Laboratories (USA), SCID mice were from Massachusetts General Hospital (USA) and BALB/c mice were from Charles River (USA).

Synthesis

TNP-470 was conjugated to HPMA copolymer-Gly-Phe-Leu-Gly-ethylendiamine via nucleophilic attack on the α-carbonyl on the TNP-470 releasing the chlorine. Briefly, HPMA copolymer-Gly-Phe-Leu-Gly-ethylendiamine (100 mg) was dissolved in DMF (1.0 ml). Then, TNP-470 (100 mg) was dissolved in 1.0 ml DMF and added to the solution. The mixture was stirred in the dark at 4° C. for 12 h. DMF was evaporated and the product, HPMA copolymer-TNP-470 conjugate was redissolved in water, dialyzed (10 kDa MWCO) against water to exclude free TNP-470 and other low molecular weight contaminants, lyophilized and stored at −20° C. Reverse phase HPLC analysis using a C18 column, was used to characterize the conjugate.

Bovine Capillary Endothelial (BCE) Cell Proliferation Assay

BCE cells were obtained and grown as previously described[48]. For the proliferation assay, cells were washed with PBS and dispersed in a 0.05% trypsin solution. Cells were suspended (15,000 cells/ml) in DMEM supplemented with 10% BCS and 1% OPS, plated onto gelatinized 24-well culture plates (0.5 ml/well), and incubated for 24 h (37° C., 10% $CO_2$). The media was replaced with 0.25 ml of DMEM, 5% BCS and 1% GPS and the test sample applied. Cells were challenged with free or conjugated TNP-470 (10 pg/ml to 1 µg/ml TNP-470-equivalent concentration). After 30 min of incubation, media and bFGF were added to obtain a final volume of 0.5 ml of DMEM, 5% BCS, 1% GPS and 1 ng/ml bFGF. Control cells were grown with or without bFGF. After 72 hr, cells were dispersed in trypsin, resuspended in Hematall (Fisher Scientific, Pittsburgh, Pa.), and counted in a Coulter counter.

Chick Aortic Ring Assay

Aortic arches were dissected from day-14 chick embryos, cut into cross-sectional fragments, and implanted in vitro in Matrigel using a modification of methods previously described (V. Muthukkaruppan, personal communication). When cultured in MCDB-131 medium supplemented with 5% fetal bovine serum, endothelial cells sprouted and vascular channel formation occurred within 24-48 hours. Free or conjugated TNP-470 (10 pg/ml to 1 µg/ml) was added to the culture.

Hepatectomy Model

Male C57BL/6J mice underwent a partial hepatectomy through a midline incision after general anesthesia with isoflourane[33]. Free or conjugated TNP-470 (30 mg/kg) were given s.c. every other day for 8 days beginning on the day of surgery according to the scheme described in FIG. 4a. Alternatively, the doses given were 60 mg/kg the day of surgery and 4 days later or 120 mg/kg once on the day of the partial hepatectomy. The liver was harvested on the $8^{th}$ day, weighed and analyzed by histology.

Evaluation of the Body Distribution of Free TNP-470 and HPMA copolymer-TNP-470 in Mice Bearing s.c. LLC Male C57BL/6J mice were inoculated with 5×10⁶ viable LLC cells s.c. and the tumor was allowed to grow to a volume of approximately 100 mm³. Animals were injected i.v. with free or conjugated TNP-470 (30 mg/kg). Intracerebral withdrawal of CSF from the brain of C57BL/6J mice was performed using a Model 310 stereotaxic apparatus (Stoelting Co., Wooddale Ill.) according to stereotaxic coordinates described in the mouse brain atlas[49] and the method described in Waynforth[50]. Once the desired amount of fluid was obtained (approximately 20 µl), the animal was euthanized via cervical dislocation at times up to 72 h. Tumors, major organs, blood, urine and CSF were collected and homogenized. Then TNP-470 was extracted in chloroform. Following evaporation of the chloroform, samples were redissolved and high-performance liquid chromatography (HPLC)/tandem Mass Spectrometry (LC-MS/MS) was used to determine the amount of free TNP-470 in the samples as previously described[36].

Evaluation of Antitumor Activity of HPMA Copolymer-TNP-470

Male C57BL/6J mice (~8 weeks, ~20 g) were inoculated with 5×10⁶ viable LLC or A2058 melanoma cells s.c. The tumors were allowed to grow to a volume of approximately 100 mm³. Animals were injected i.v. with free TNP-470 or HPMA copolymer-TNP-470 (30 mg/Kg TNP-equiv.) or saline (250 µl i.v.). Each group consisted of 5 mice. Mice were euthanized when tumors reached or surpassed a size equivalent to 30% of their body weight. Animals were weighed daily and observed for signs of tumor progression and euthanized if their body weight decreased below 80% of their starting weight. Animals were monitored for general health, weight loss, and tumor progression. At termination, mice underwent post-mortem examination and tumors were dissected and weighed. A similar experiment was repeated in which treatment with escalating doses of the conjugate was initiated when tumors reached 500 mm$^3$. The same dosing schedule was repeated with white SCID male mice (~8 weeks, ~20 g) inoculated with 5×10$^6$ viable A2058 human melanoma cells s.c. and treated as described above.

Statistical Methods

All of the in vitro data are expressed as the mean±standard deviation of the mean (S.D.). All of the in vivo data are expressed as the mean±standard error of the mean (S.E.). Statistical significance was assessed using the Student's t-test. P values of 0.05 or less were considered statistically significant.

Results

Synthesis and Characterization

Figure 1B:
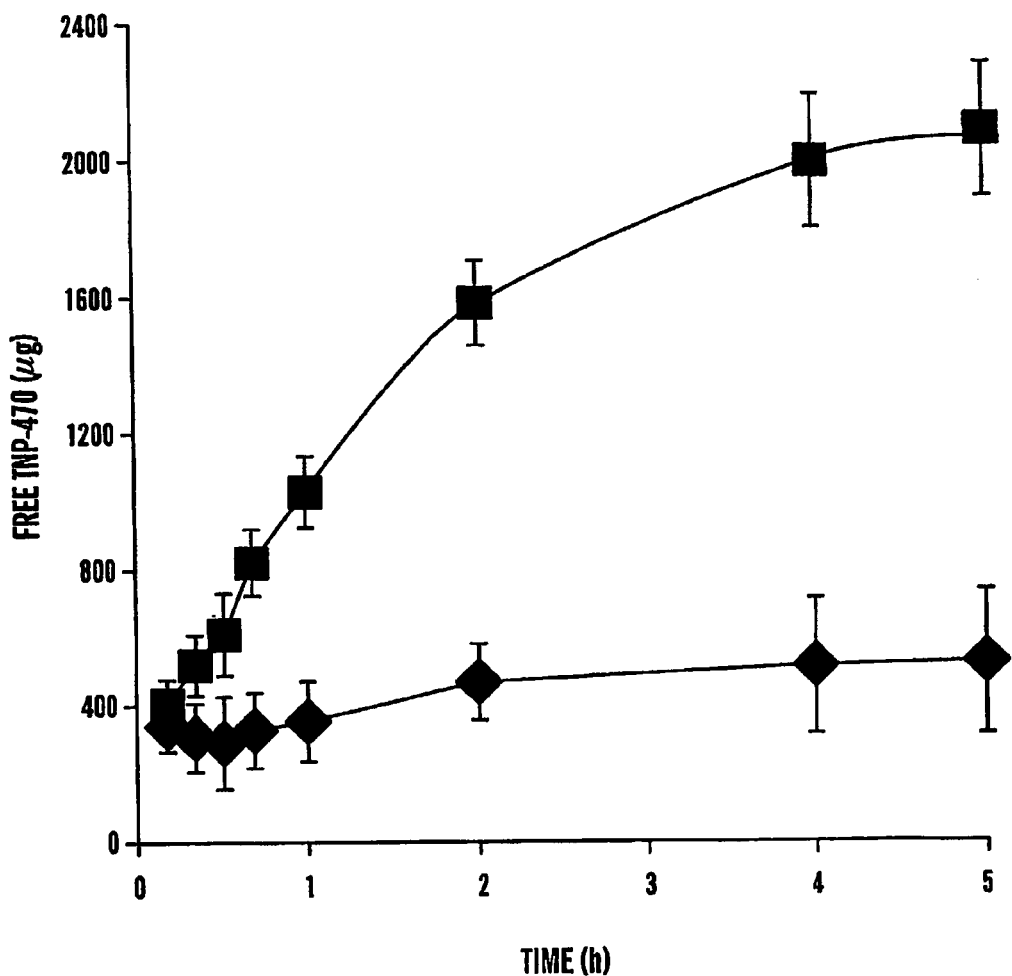
FIG. 1B shows in vitro release of TNP-470 from HPMA copolymer in the presence (-■-) and absence (-♦-) of cathepsin B.

HPMA copolymer-Gly-Phe-Leu-Gly-ethylenediamine-TNP-470 conjugate (FIG. 1A) was synthesized, purified and characterized by HPLC. Gly-Phe-Leu-Gly polymer-TNP-470 linker was designed to permit intralysosomal TNP-470 liberation due to action of the lysosomal cysteine proteases[29], such as cathepsin B. It has been shown that cathepsin B is overexpressed in many tumor cells[30]. The conjugate accumulates selectively in the tumor tissue due to the EPR effect and is slowly internalized into endothelial cells in the tumor bed by fluid-phase pinocytosis. The conjugate should not internalize into normal quiescent endothelial cells, hence will not be exposed to lysosomal enzymes leaving the linker intact. Free TNP-470 eluted as a single peak with a retention time of 13.0 min while the conjugate eluted as a wider peak at 10.0 min (results not shown). Free drug was negligible (<0.01% of total TNP-470) following repeated purification by dialysis. TNP-470 is not water-soluble but became soluble following conjugation with HPMA copolymer. The conjugate was stable for three days in phosphate buffered saline or citrate buffer, pH 5.5, 0.2 M at 37° C. However, under the same conditions with the addition of the lysosomal enzyme cathepsin B, the linker between the polymer and the drug (Gly-Phe-Leu-Gly[31]) was cleaved and TNP-470 was released (FIG. 1B). These conditions imitate the lysosomal environment in endothelial cells where lysosomal enzymes, such as cathepsin B, are present. TNP-470 release from the conjugate reached a plateau within 5 h of incubation with cathepsin B and did not increase appreciably even after 5 days. The incubated solution was then analyzed and had a TNP-470 content of approximately 10 mol %. We next tested the HPMA copolymer-TNP-470 conjugate activity in two in vitro angiogenesis assays: the endothelial cell proliferation and the chick aortic ring assays.

Bovine Capillary Endothelial (BCE) Cell Proliferation

Figure 2A:
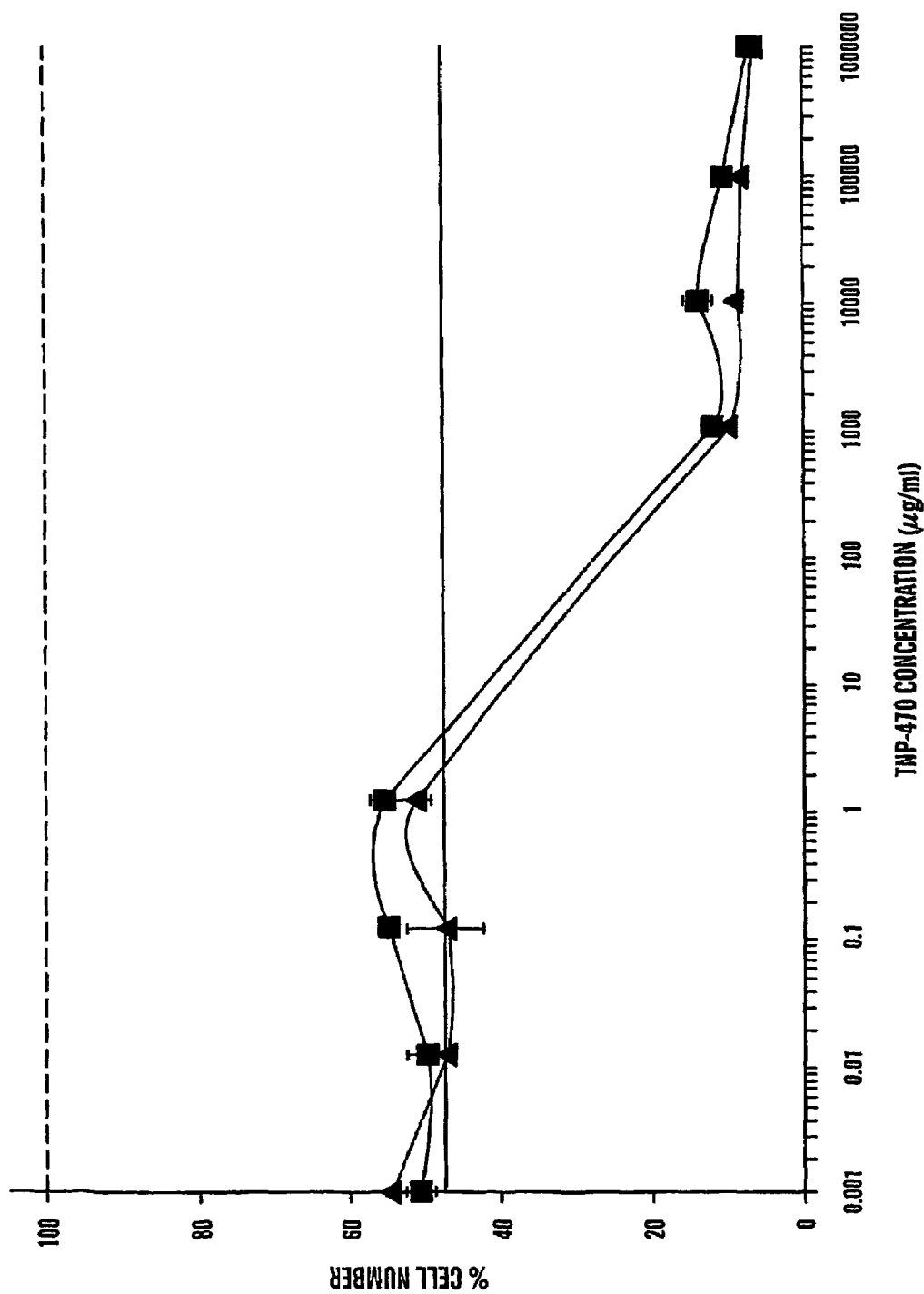
FIG. 2A shows inhibition of BCE proliferation in vitro after 72 h. TNP-470 (-▲-) and HPMA copolymer-Gly-Phe-Leu-Gly-en-TNP-470 (-■-) had similar cytostatic effect on bFGF-induced proliferation of endothelial cells at doses lower than 1 µg/ml and cytotoxic effect at doses higher than 1 µg/ml. The dotted line represents the proliferation of bFGF-induced BCE cells ( - - - ) and the solid line represents the BCE cell proliferation in the absence of bFGF (-).

To determine if HPMA copolymer-TNP-470 was active in endothelial cells we tested its inhibitory effect on BCE cell proliferation in vitro. BCE cell growth, stimulated by bFGF, was inhibited similarly by TNP-470 and HPMA copolymer-TNP-470 (FIG. 2A). Both free and conjugated TNP-470 inhibited bFGF-induced proliferation (cytostatic effect) of BCE cells from 10 pg/ml to 1 µg/ml TNP-470-equivalent concentration. However, at doses higher than 1 µg/ml both free and conjugated TNP-470 were cytotoxic. These data are in agreement with published results of free TNP-470 on different endothelial cells[11,32].

Chick Aortic Ring Assay

Figure 2B:
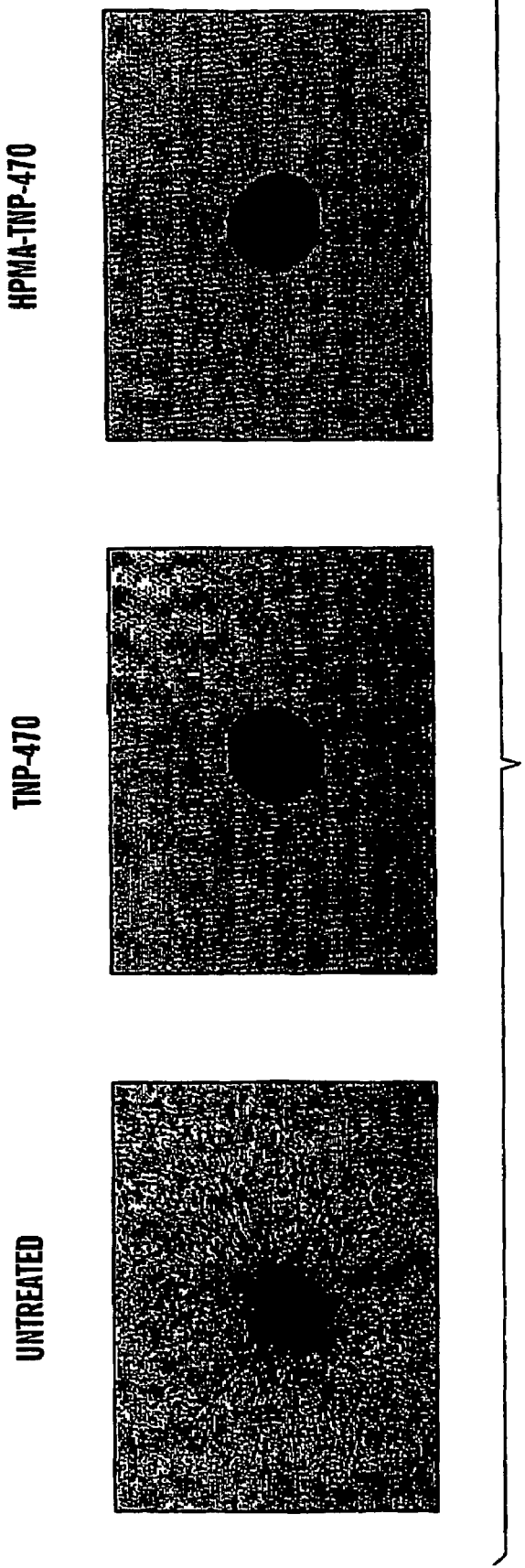
FIG. 2B shows the chick aortic ring endothelial sprouting assay. The effect of TNP-470 (central panel) and HPMA copolymer-Gly-Phe-Leu-Gly-en-TNP-470 (right panel) at 100 pg/ml TNP-470 equivalent-dose are shown; and a control chick aortic ring (left panel) with abundant sprouting.

Having demonstrated that the conjugate inhibited in vitro endothelial cell growth, an ex-vivo model of chick aortic rings implanted in Matrigel was utilized to further characterize the HPMA copolymer-INP-470 conjugate. Both free and conjugated TNP-470 reduced the number and length of vascular sprouts growing from the chick aortic ring at 50 pg/ml and completely prevented outgrowth at 100 pg/ml (FIG. 2B). A control aortic ring (left panel) showed abundant sprouting. Similar dose dependency was found for free TNP-470 in a mouse aortic ring assay (Moulton, unpublished results).

Hepatectomy

We have shown that HPMA copolymer-TNP-470 was equally-active as the free TNP-470 in vitro. Therefore, we evaluated its antiangiogenic activity in vivo.

Figure 3A:
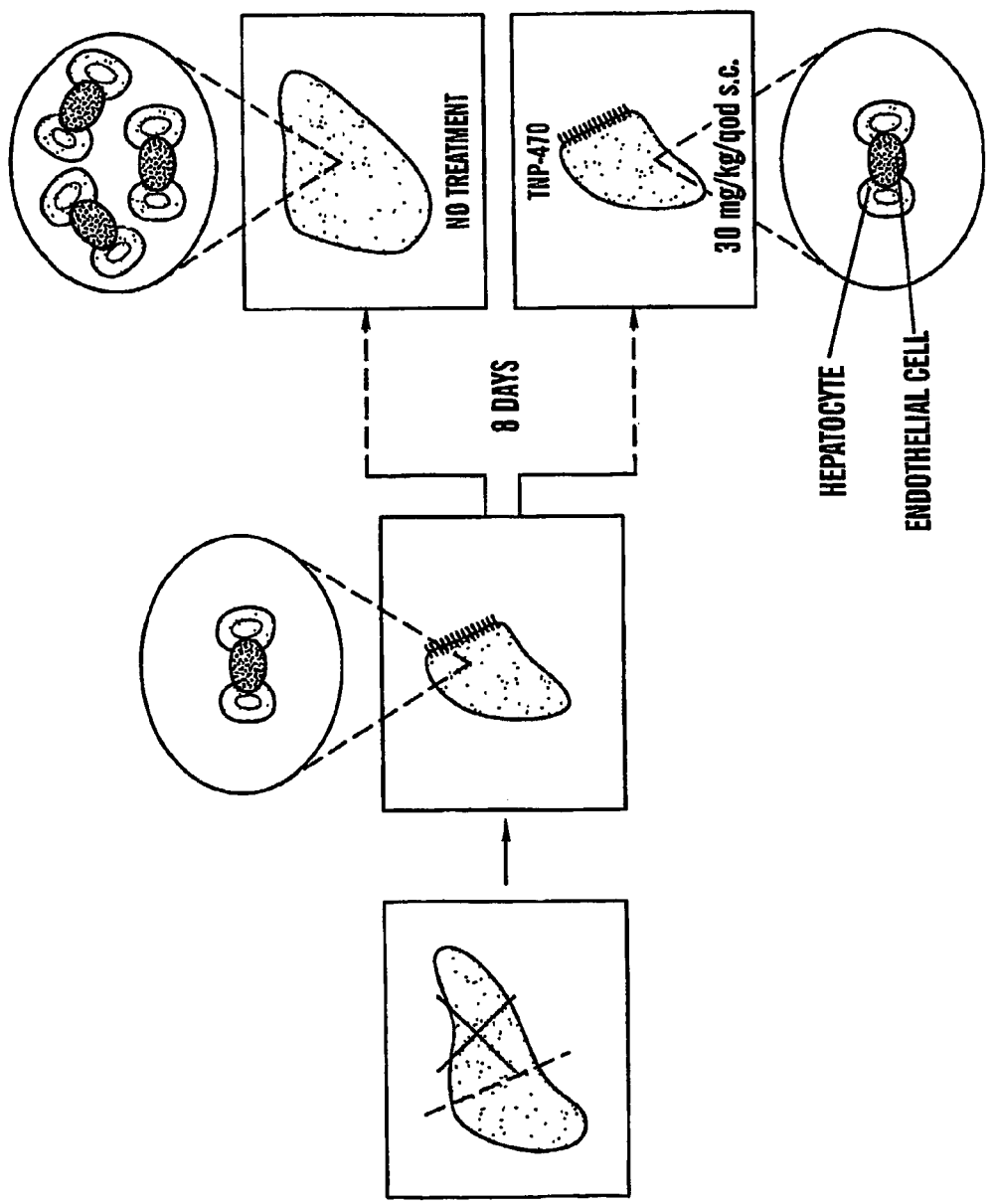
FIG. 3A shows a schematic representation of the hepatectomy model. Untreated livers regenerate in 8 days, but they do not regenerate when treated with TNP-470 30 mg/kg/q.o.d s.c.
Figure 3B:
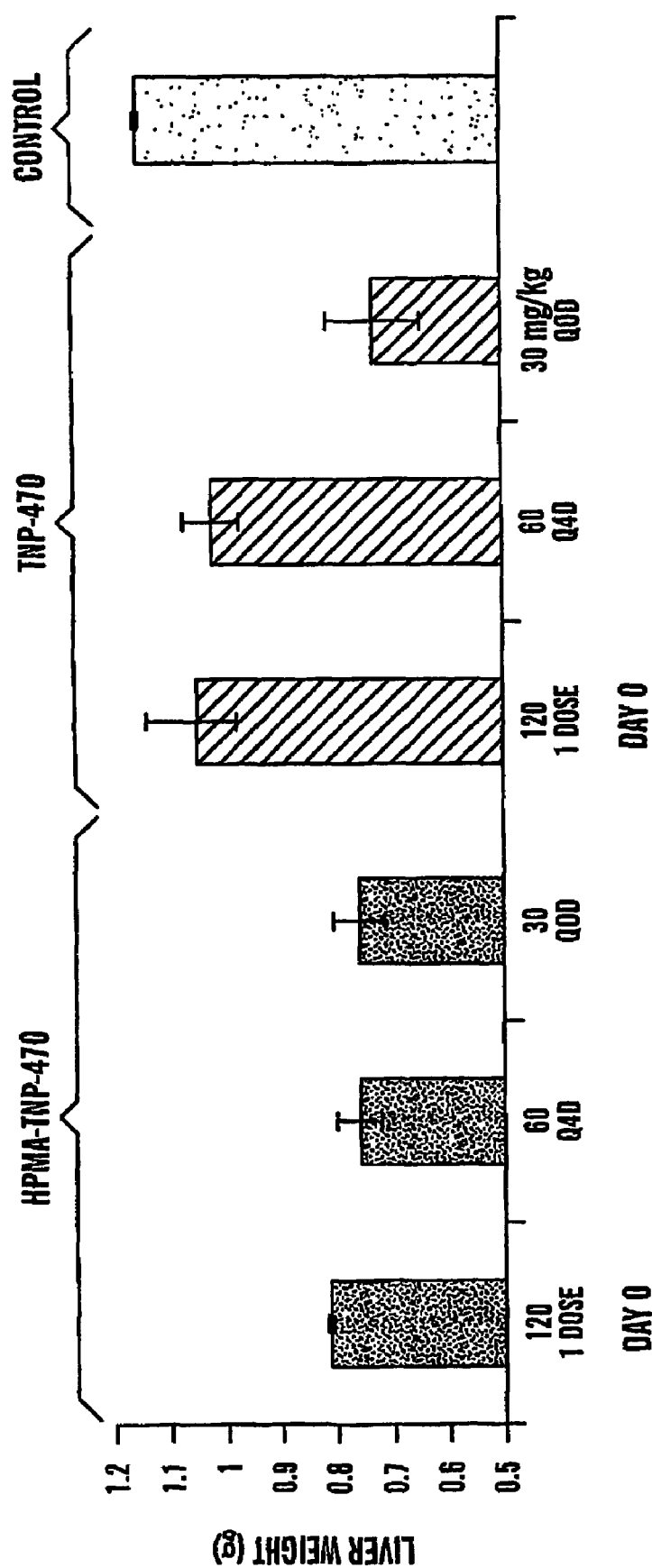
FIG. 3B shows that free TNP-470 (stripes columns) inhibited liver regeneration when used at 30 mg/kg/q.o.d s.c. However, it did not inhibit liver regeneration at other dosing schedules. Conjugated TNP-470 (solid columns) inhibited liver regeneration at 30 mg/kg/q.o.d s.c. or 60 mg/kg/q.2.d s.c. or even at a single dose of 120 mg/kg/day of operation s.c. compared to the control regenerated group (dotted columns).

Before testing the conjugate in tumor models in vivo, we established the efficacy of HPMA copolymer-TNP-470 conjugate in the hepatectomy model (FIG. 3A). This non-neoplastic model is a relatively fast (8 days) in vivo angiogenesis-dependent process[33]. We employed the hepatectomy model to compare the endothelial cell inhibitory activity of free and conjugated TNP-470, because liver regeneration post hepatectomy is angiogenesis-dependent, similar to tumor growth[33,34]. Following partial hepatectomy, control mice regenerated their resected liver to their pre-operative mass (~1.2 g) by post-operative day 8 (FIG. 3B). In mice treated subcutaneously (s.c.) with free TNP-470 or its polymer-conjugated form at 30 mg/kg every other day (q.o.d), the regeneration of the liver was inhibited and livers reached the average size of 0.7 g on post-operative day 8 (FIG. 3B). Free TNP-470 did not inhibit liver regeneration when injected at 60 mg/kg every four days or at a single injection of 120 mg/kg at the day of the hepatectomy. However, HPMA copolymer-TNP-470 conjugate had an equivalent effect as the 30 mg/kg q.o.d. dosing schedule when given every 4 days (q.4.d.) at 60 mg/kg or at a single dose of 120 mg/kg on the day of hepatectomy. This suggests that the conjugate has a longer circulation time than the free TNP-470 in vivo and/or that the conjugate accumulates at the site of proliferating endothelial cells, leading to sustained release of TNP-470 from the polymer. Because liver regeneration is regulated by endothelial cells[33,34], it was expected that a similar effect would occur with proliferating endothelial cells in tumor tissue, where the conjugate accumulates due to the EPR effect.

Early Mouse Development

Figure 3C:
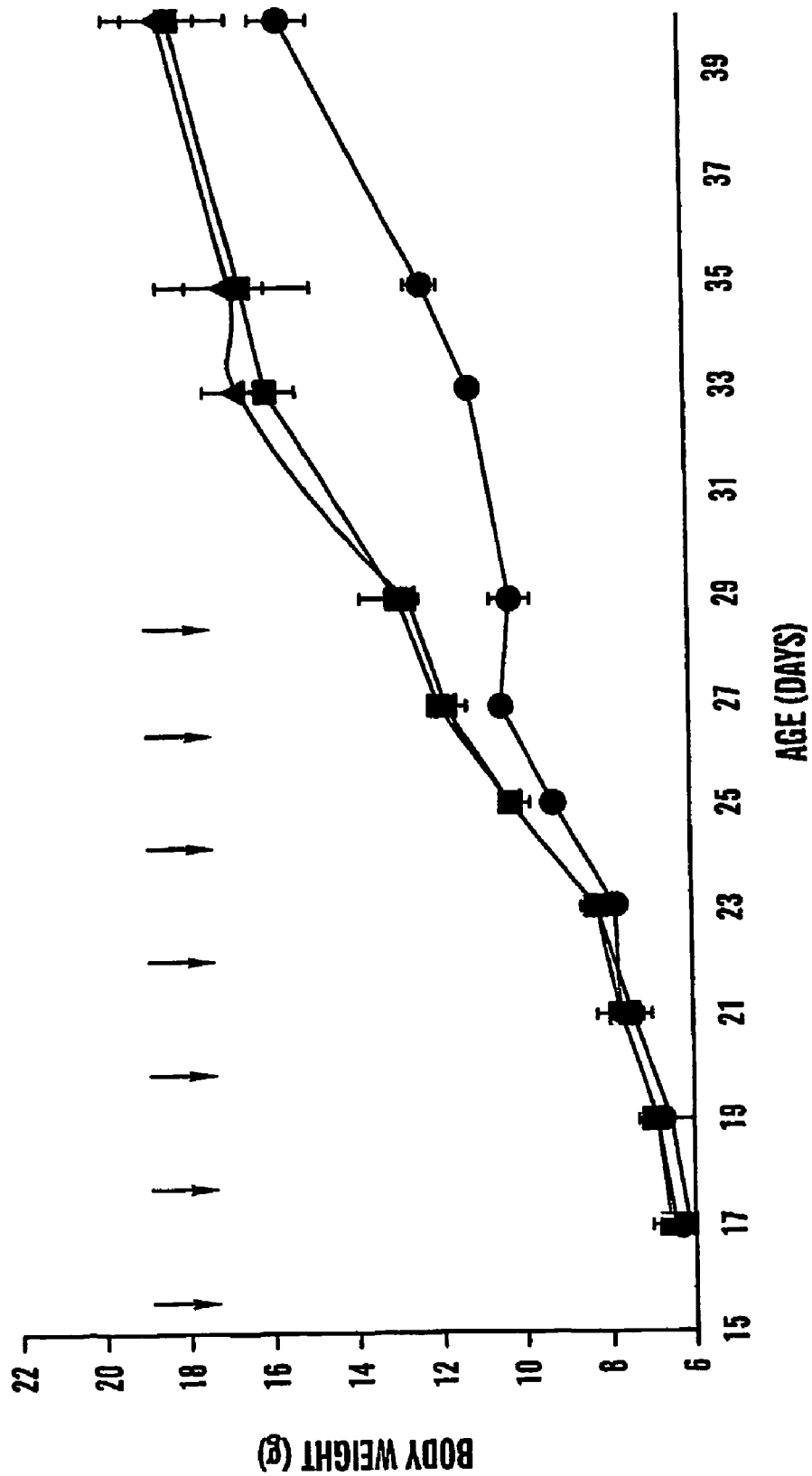
FIG. 3C shows that free TNP-470 (-●-) causes delay in newborn mice development, but did not affect body weight when used in the conjugated form (-▲-) similar to the control mice (-■-). Arrows represent days of treatment. Data represent mean±SE, n=9 mice per group.

Free and conjugated TNP-470 were injected into 7 and 17 day-old BALB/c mice in order to test their effects on normal development. Free TNP-470 inhibited growth, by inhibiting weight gain at this critical age. However, HPMA copolymer-TNP-470 conjugate-treated mice developed similarly to the control group injected with saline (FIG. 3C). These results differed from the results obtained from the hepatectomy experiments. HPMA copolymer-TNP-470 conjugate inhibited liver regeneration following hepatectomy but did not inhibit normal development in the newborn mice. A possible explanation is that the conjugate extravasated through leaky vessels in the liver following surgery (i.e., same inhibition as seen in wound healing delayed by TNP-470[35]). However, the conjugate did not leak from normal vessels developing in the newborn.

Figure 4A:
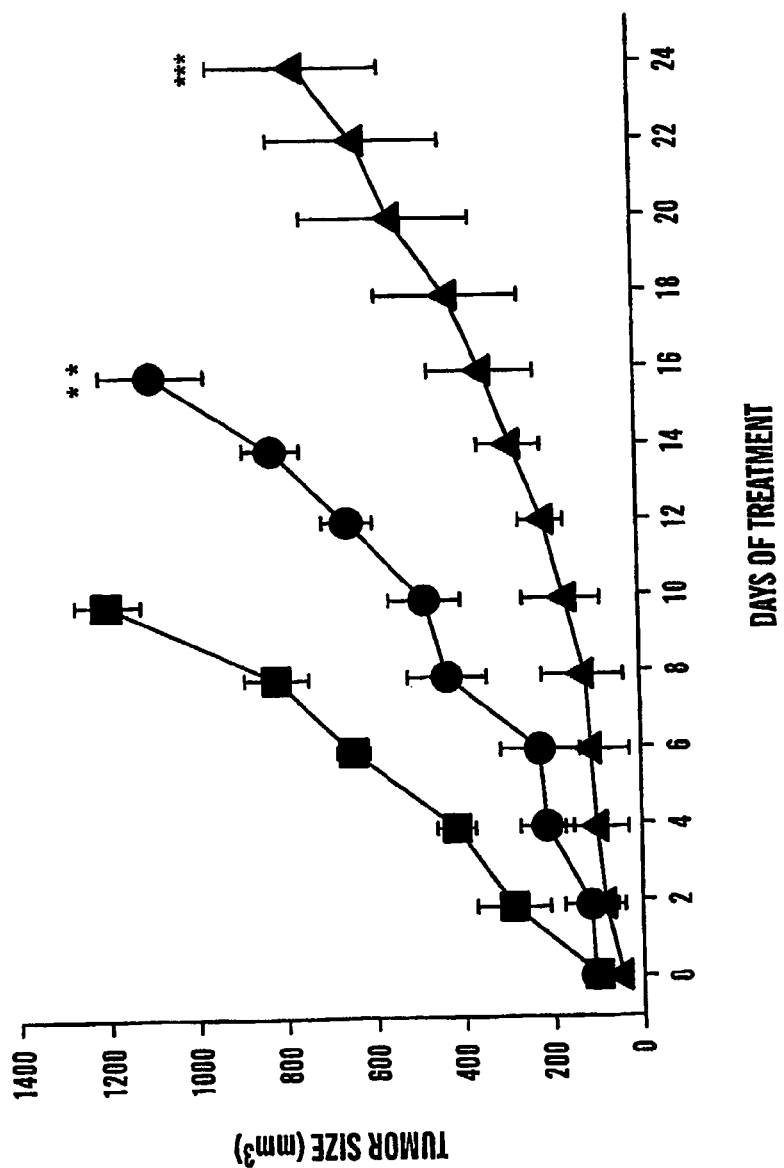
FIG. 4A shows the effect of TNP-470 (-●-); HPMA copolymer-Gly-Phe-Leu-Gly-en-TNP-470 (-▲-); and control mice (-■-) on tumors. Data represent mean±SE, n=8 mice per group. P values of <0.05 were marked as *, P<0.03, P<0.01*.
Figure 4B:
FIG. 4B shows SCID mice and excised tumors correlating to panel (A) at day 8 of treatment.
Figure 4C:
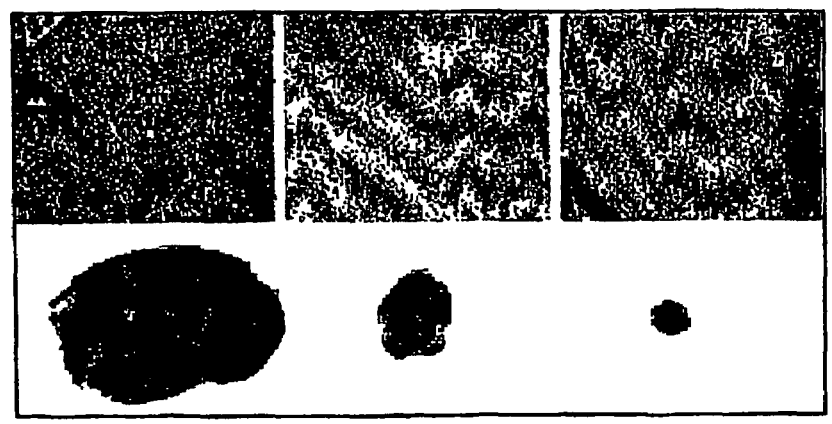
FIG. 4C shows H & E staining of tumors excised from animals in different groups on day 8 at high and low power.

Evaluation of Antitumor Activity of HPMA Copolymer-TNP-470 on SCID Mice Bearing s.c. A2058 Human Melanoma Mice bearing s.c. A2058 melanoma showed increased survival when treated with free and conjugated TNP-470 (T/C=0.34 for TNP-470 and 0.12 for the conjugate) (FIG. 4A). T/C was defined as the ratio of the mean volume of tumor of the treated animals (T) divided by the mean volume of tumor of the untreated control group (C). During this study there were neither deaths due to toxicity nor weight loss in the mice treated with the conjugate, indicating dose escalation of the conjugate to be possible. A significant decrease in tumor growth rate was observed in animals treated with TNP-470 ($P<0.03$) and with HPMA copolymer-TNP-470 ($P<0.05$) compared to controls (FIG. 4A, B, C). FIG. 4C presents histological sections of tumors representing the three treated groups (saline, free or conjugated TNP-470) stained with H & E and showing viable tumor cells in all.

Figure 5A:
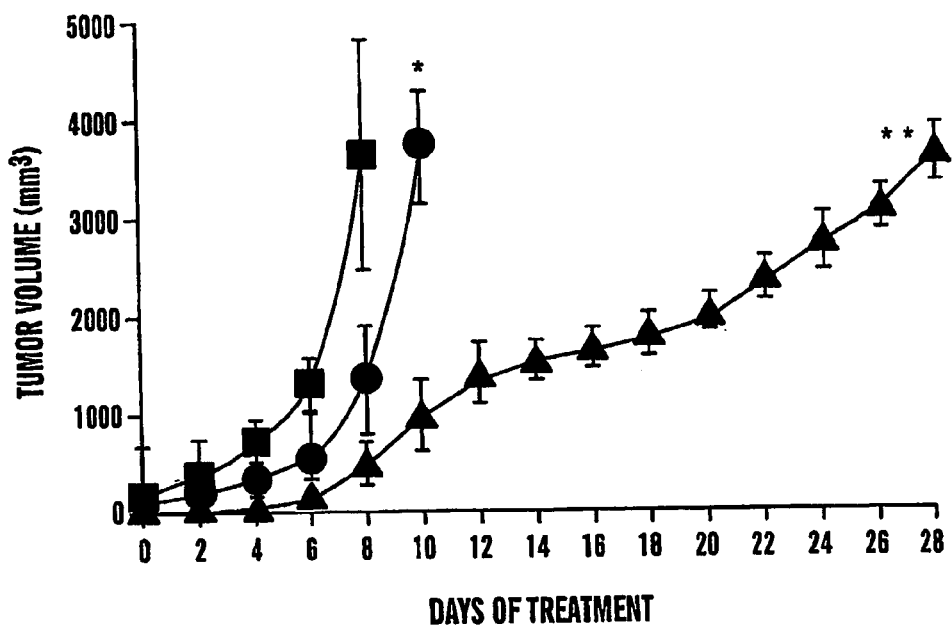
FIG. 5A shows the effect of TNP-470 at 30 mg/kg/q.o.d. s.c. (-●-); HPMA copolymer-Gly-Phe-Leu-Gly-en-TNP-470 at 30 mg/kg/q.o.d. s.c. (-▲-) on tumor growth; control mice (-■-) are also shown. Data represent mean±SE, n=10 mice per group.
Figure 5B:
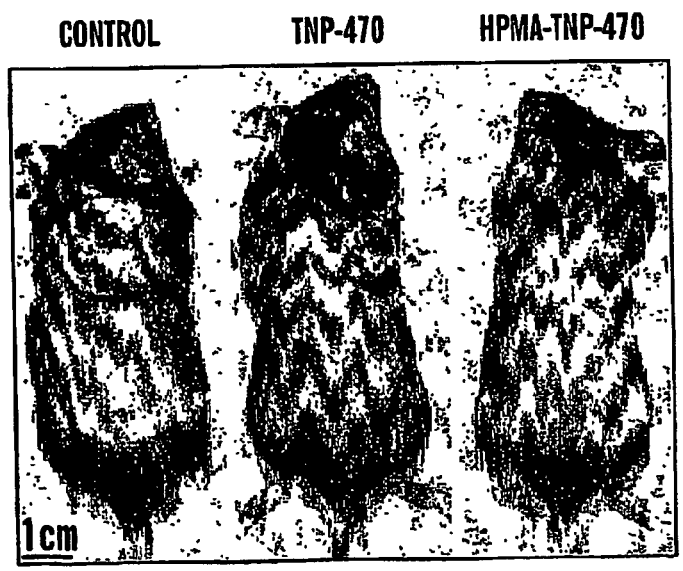
FIG. 5B shows representative C57 mice correlating to (A) on day 10 following treatment.
Figure 5C:
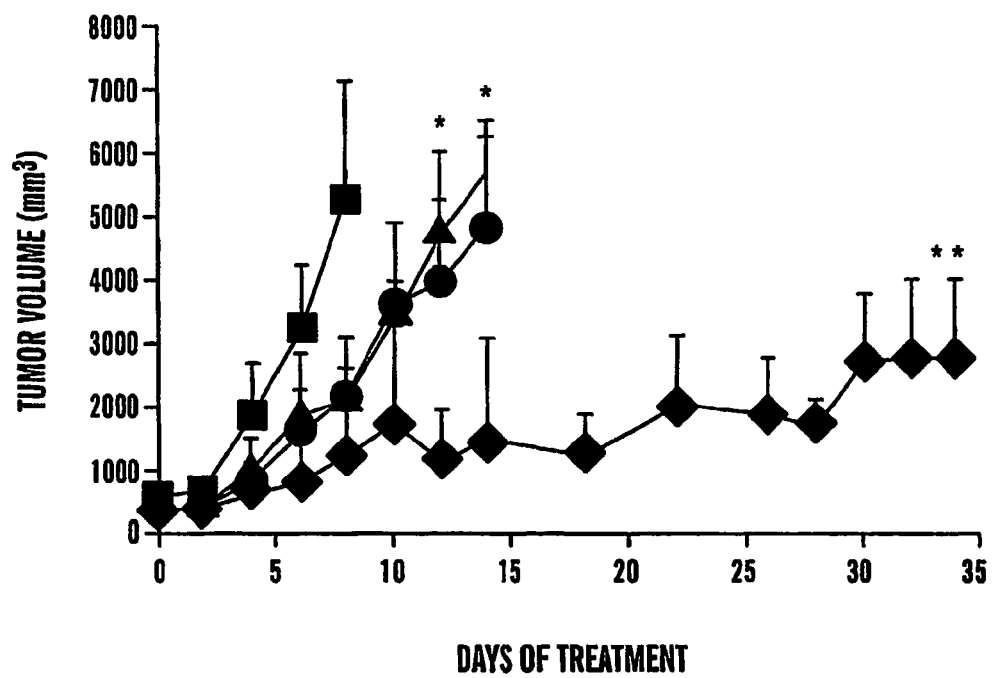
FIG. 5C shows dose escalation of HPMA copolymer-Gly-Phe-Leu-Gly-en-TNP-470: at 30 (-▲-), at 60 (-●-) and at 90 mg/kg/q.o.d. (-♦-) and control mice (-■-) are shown. Data are mean±SE, n=10 mice per group.
Figure 5D:
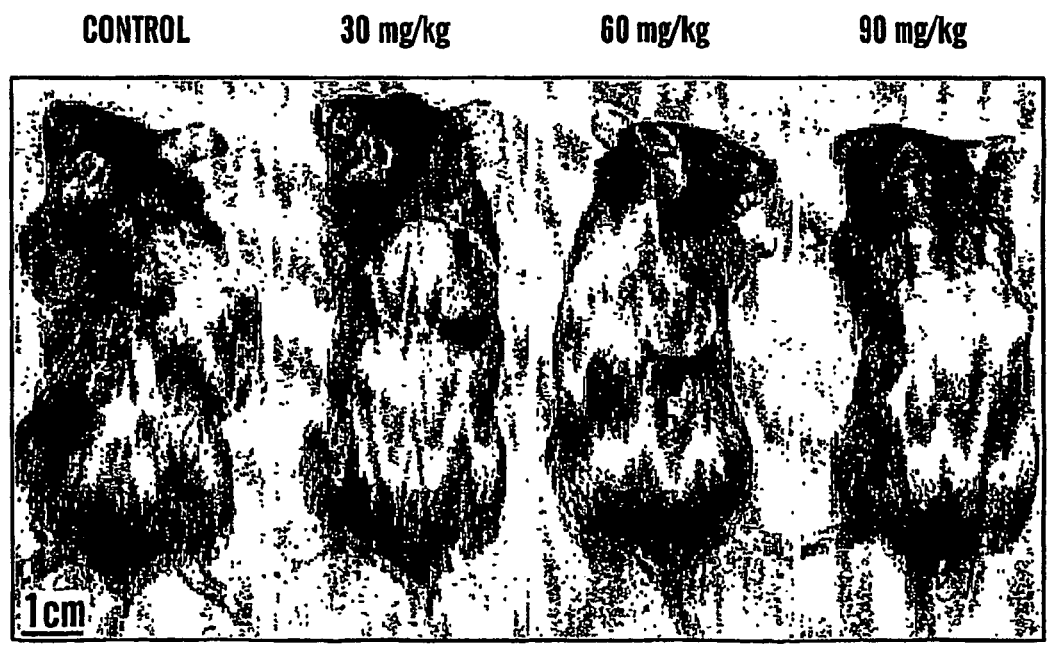
FIG. 5D shows C57 mice correlating to (C). P values of <0.05 were marked as *, P<0.03 as , P<0.01 as *.

Evaluation of Antitumor Activity of HPMA Copolymer-TNP-470 on C57BL/6J Mice Bearing s.c. LLC Mice bearing s.c. LLC showed increased survival when treated with free and bound TNP-470 at equivalent concentration of TNP-470 of 30 mg/kg q.o.d. HPMA copolymer-TNP-470 exhibited superior antitumor activity compared to free TNP-470. On day 8, when control mice were sacrificed, HPMA copolymer-TNP-470 inhibited tumor growth by 86% ($P<0.03$) whereas free TNP-470 by 67% ($P<0.05$) (FIG. 5A,B). In addition, the conjugate did not induce weight loss whereas free TNP-470 did (data not shown). Since HPMA copolymer-TNP-470 did not induce weight loss, we tested the conjugate in LLC-bearing mice at the higher doses of 60 and 90 as well as 30 mg/kg/q.o.d. The conjugate inhibited tumor growth equally at 30 or 60 mg/kg/q.o.d ($P<0.03$, T/C=0.4, day 8). Tumor suppression was significantly enhanced at 90 mg/kg/q.o.d ($P<0.05$, T/C=0.24, day 8) (FIG. 5C, D). Even at the higher dose of 90 mg/kg/q.o.d., there was no animal weight loss, indicating we did not reach the maximum tolerated dose (MTD). Free TNP-470 at these doses is known to be toxic to the mice. In this set of experiments treatment was started when tumors reached 500 mm$^3$, therefore results differed from previous experiments where treatment started when tumors were 100 mm$^3$.

Evaluation of TNP-470 and HPMA Copolymer-TNP-470 in the Cerebrospinal Fluid of Mice Bearing s.c. LLC HPLC-Mass spectrometry (LC-MS/MS) showed that free TNP-470 is present in the cerebrospinal fluid (CSF) of mice with s.c. LLC tumor following i.v. administration of the drug. However, when HPMA copolymer-TNP-470 conjugate was injected, neither TNP-470 nor its known metabolites[36] were detected in the CSF. These results suggest that TNP-470-related neurotoxicity could be avoided when TNP-470 is conjugated to HPMA copolymer. Full body distribution and pharmacokinetics of free and conjugated TNP-470 in normal tissues, blood, urine and tumor analyzed by LC-MS/MS will be published separately.

Conclusions

Although a new departure in cancer therapy, several polymer-drug conjugates are already in early clinical trials[37]. These include HPMA copolymer-doxorubicin (PK1, FCE28068), HPMA copolymer-paclitaxel (PNU 166945), HPMA copolymer-camptothecin, polyethylene glycol (PEG)-camptothecin, polyglutamic acid-paclitaxel, an HPMA copolymer-platinate (AP5280) and also an HPMA copolymer-doxorubicin conjugate bearing additionally galactosamine (PK2, FCE28069)[38]. Reduced toxicity and activity in chemotherapy refractory patients has been described. In phase I, PK1 displayed a maximum tolerated dose of 320 mg/m$^2$ (compared to 60 mg/m$^2$ for free doxorubicin) and also showed antitumor activity[39]. Moreover, the clinical pharmacokinetics (PK1 $t_{1/2\alpha}$=1.8 h with no dose dependency of clearance compared to few minutes for free doxorubicin) were very similar to those reported in animals[25]. PK1 has proven ability to target solid tumors by the EPR effect[40] with concomitant renal elimination resulting in low blood levels within 1-5 h in animals and in humans[25,39].

Polymer-angiogenesis inhibitor conjugates can capitalize on the ability of macromolecules to target solid tumor tissue passively by the EPR effect[26] (similar to PK1). This effect occurs due to the poorly organized tumor vasculature[41] resulting in 'enhanced permeability' towards circulating molecules. The poor lymphatic drainage in tumor tissue leads to increased 'retention'. It is accepted that the main reason for the improved antitumor activity of the polymer-drug conjugates, with respect to the free drug, is tumor targeting as a result of this EPR effect[37]. Gly-Phe-Leu-Gly polymer-TNP-470 linker used in this study was designed to permit intralysosomal TNP-470 liberation due to action of the lysosomal cysteine proteases[29]. In order to exert an antitumor effect, an active TNP-470 species must be released at the tumor site and interact with methionine aminopeptidase 2 (MetAP2) in endothelial cells. MetAP2 is one molecular target of TNP-470 that was recently identified, although the precise mechanism underlying its selective effect on the proliferation of endothelial cells is yet to be understood[42]. Therefore, the T/C values for the conjugate of 0.12-0.14 indicated that TNP-470, which was bound to the polymeric backbone during circulation, was released at the tumor site. The mechanism for release of a TNP-470 moiety involves cellular uptake, followed by enzymatic cleavage of the peptide linker within the lysosomes of endothelial cells. It is likely that some of the conjugate that accumulates in the tumor will be taken up by tumor cells. However, a higher concentration of TNP-470 will be needed to affect tumor cells (3-logs higher).

Many studies of angiogenesis inducers and inhibitors rely on in vitro or in vivo models as indicators of efficacy. However, as valuable as these models are, there are limitations to each one of these. Therefore, multiple assays used, involving both in vitro and in vivo assays, are at present the best way to minimize the problems inherent in any specific assay[43]. In this way, a proper evaluation and comparison between free and conjugated TNP-470, was achieved.

In summary, we have shown that tumor growth rate can be significantly reduced by systemic delivery of an antiangiogenic agent that is targeted to the tumor vasculature. In addition, this conjugate likely leads to reduced toxicity and does not cause weight loss in newborn and adult mice because, unlike the free form, it does not enter the CSF. The enhanced and long acting effect of the conjugate compared to that of the free TNP-470 (as described in the hepatectomy model), can be ascribed to increased accumulation in neovascularized tissues and to greater stability of the conjugate. Several components of this strategy contribute to its pronounced antitumor activity, which may facilitate future therapy in humans. First, the HPMA copolymer used in this study has multivalent side-chains, which make it possible to target high loading of TNP-470 or other drugs to angiogenic blood vessels due to the EPR effect. Second, it is feasible to conjugate an endothelial cell targeting moiety to those side-chains on the polymeric backbone[44]. Third, we emphasize that; (a) angiogenesis inhibitors suppress endothelial growth from inside the vascular lumen and may also traverse leaky tumor vessels; (b) the conjugate HPMA copolymer-TNP-470 provides prolonged exposure of the drug to endothelium; and (c) the conjugated TNP-470 cannot cross normal blood brain barrier. Lastly, polymers are less immunogenic than viral vectors and are known to decrease or even abrogate immunogenicity of bound proteins and to prolong circulation time[24,45]. Polymer-enzyme conjugates such as polyethylene glycol (PEG)-L-asparaginase (Oncaspar®) for the treatment of acute lymphoblastic leukemia have been FDA approved and has become commercially avaliable[46]. Therefore, it may be feasible to deliver therapeutic genes or proteins repeatedly to angiogenic blood vessels for sustained treatment of diseases that depend on angiogenesis and vascular remodeling. This study represents an example of how an effective angiogenesis inhibitor can be significantly improved and its toxicity decreased by conjugating it to a polymer.

EXAMPLE 2

Miles Assay:

One of the problems with angiogenesis-dependent diseases is increased vessel permeability (due to high levels of VPF) which results in edema and loss of proteins. A decrease in vessel permeability is beneficial in those diseases. We have found, using the Miles assay (Claffey et al., Cancer Res., 56: 172-181 (1996)), that free and bound TNP-470 block permeability. Briefly, a dye, Evans Blue, was injected i.v. to anesthesized mice. After 10 minutes, human recombinant $VEGF_{165}$ was injected intradermally into the back skin. Leakage of protein-bound dye was detected as blue spots on the underside of the back skin surrounding the injection site. After 20 minutes, mice were euthanized. Then, the skin was excised, left in formamide for 5 days to be extracted and the solution read at 620 nm. Putative angiogenesis inhibitors such as free and conjugated TNP-470 were injected daily 3 days prior to the VEGF challenge. The same was repeated on tumor-bearing mice to evaluate the effect of angiogenesis inhibitors on tumor vessel permeability.

Figure 6A:
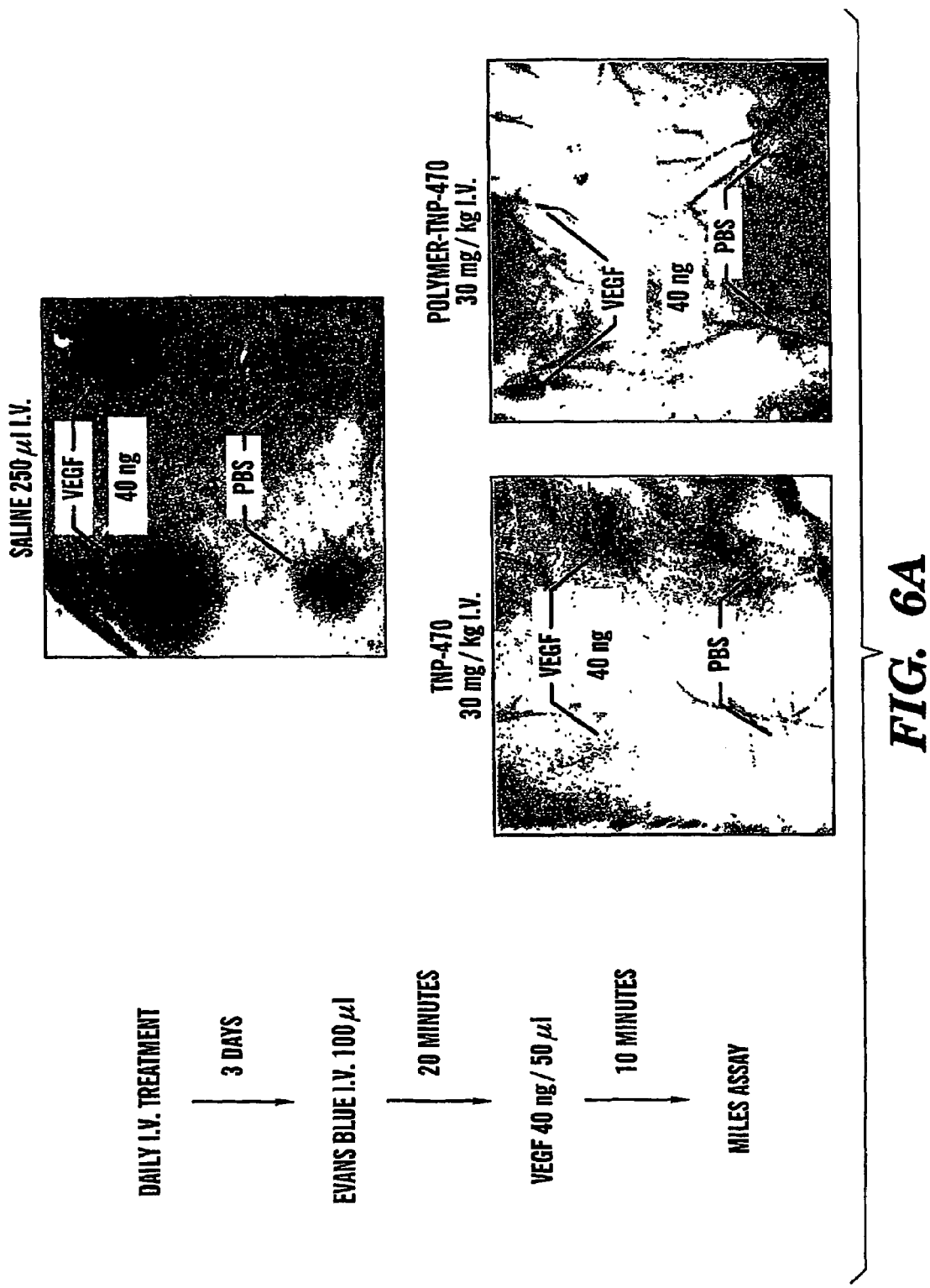
FIG. 6 shows the results of a Miles assay.
Figure 6B:
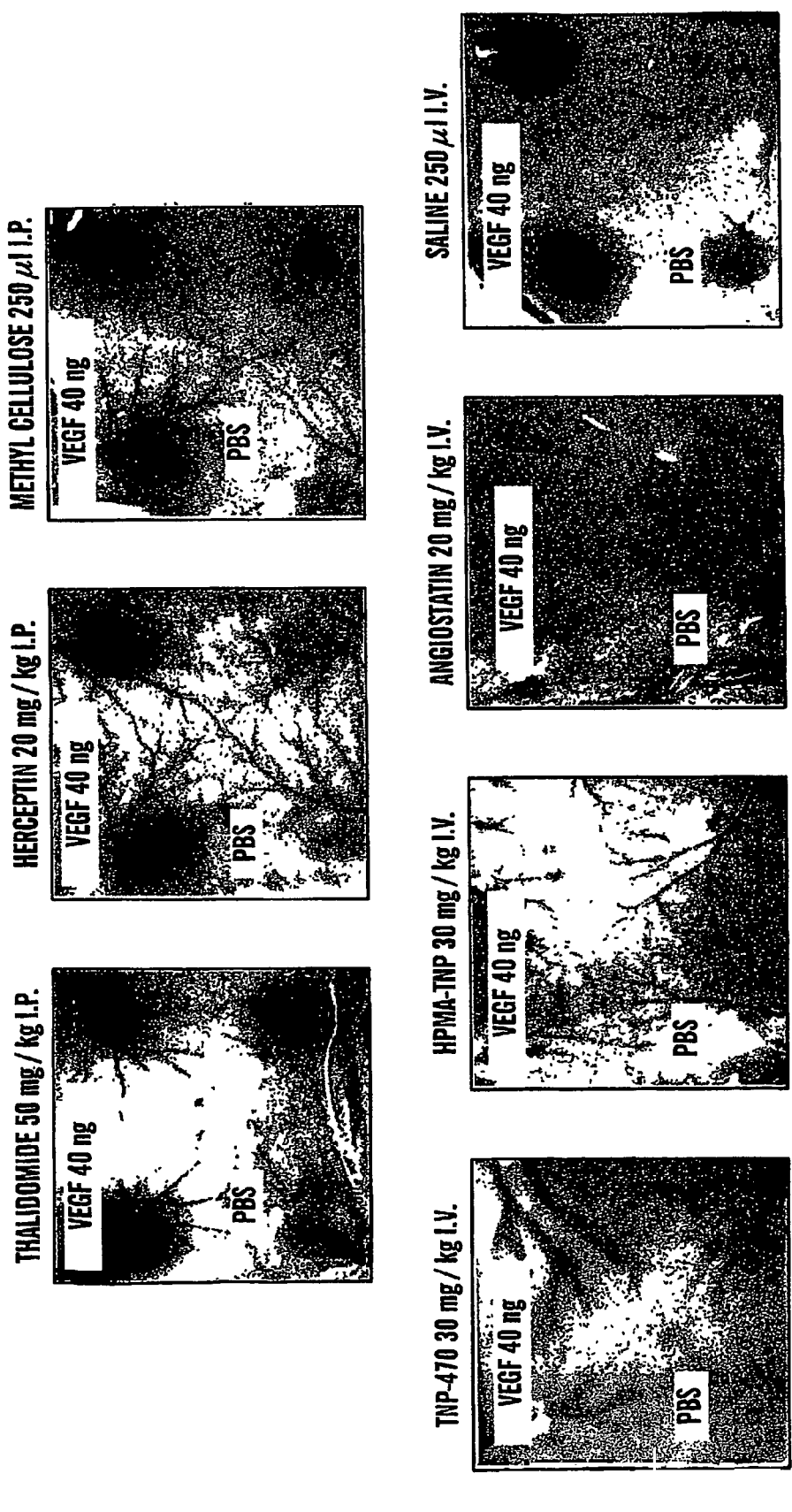

We have compared free and conjugated TNP-470 to other angiogenesis inhibitors in the Miles assay. We have found that free TNP-470 and HPMA copolymer-TNP-470 had similar inhibitory effect on VEGF induced vessel permeability as opposed to the control groups and indirect angiogenesis inhibitors such as Herceptin and Thalidomide (FIG. 6).

The references cited throughout the specification are incorporated herein by reference.

REFERENCES

1. Folkman, J. Angiogenesis. in *Harrison's Textbook of Internal Medicine* (eds. Braunwald, E. et al.) 517-530 (McGraw Hill, New York, 2001).
2. Hanahan, D. & Folkman, J. Patterns and emerging mechanisms of the angiogenic switch during tumorigenesis. *Cell* 86, 353-64 (1996).
3. Volpert, O. V. et al. Id1 regulates angiogenesis through transcriptional repression of thrombospondin-1. *Cancer Cell* 2, 473-483 (2002).
4. Folkman, J. Tumor angiogenesis. in *Cancer Medicine* (eds. Holland, J. et al.) 132-152 (B. C. Decker Inc., Ontario, Canada, 2000).
5. Lyden, D. et al. Id1 and Id3 are required for neurogenesis, angiogenesis and vascularization of tumour xenografts. *Nature* 401, 670-7 (1999).
6. Streit, M. et al. Thrombospondin-2: a potent endogenous inhibitor of tumor growth and angiogenesis. *Proc Natl Acad Sci USA* 96, 14888-93 (1999).
7. Chin, L. et al. Essential role for oncogenic Ras in tumour maintenance. *Nature* 400, 468-72 (1999).
8. Tabone, M. D. et al. Are basic fibroblast growth factor and vascular endothelial growth factor prognostic indicators in pediatric patients with malignant solid tumors? *Clin Cancer Res* 7, 538-43 (2001).
9. Yao, Y. et al. Prognostic value of vascular endothelial growth factor and its receptors Flt-1 and Flk-1 in astrocytic tumours. *Acta Neurochir (Wien)* 143, 159-66 (2001).
10. Yuan, A. et al. Aberrant p53 expression correlates with expression of vascular endothelial growth factor mRNA and interleukin-8 mRNA and neoangiogenesis in non-small-cell lung cancer. *J Clin Oncol* 20, 900-910 (2002).
11. Ingber, D. et al. Synthetic analogues of fumagillin that inhibit angiogenesis and suppress tumour growth. *Nature* 348, 555-7 (1990).
12. Antoine, N. et al. AGM-1470, a potent angiogenesis inhibitor, prevents the entry of normal but not transformed endothelial cells into the G1 phase of the cell cycle. *Cancer Res* 54, 2073-6 (1994).
13. Folkman, J. Tumor angiogenesis. in *Accomplishments in cancer research* (eds. Wells, S. J. & Sharp, P.) 32-44 (Lippincott Williams & Wilkins, New York, 1998).
14. Kudelka, A. P., Verschraegen, C. F. & Loyer, E. Complete remission of metastatic cervical cancer with the angiogenesis inhibitor TNP-470. *N Engl J Med* 338, 991-2 (1998).
15. Kudelka, A. P. et al. A phase I study of TNP-470 administered to patients with advanced squamous cell cancer of the cervix. *Clin Cancer Res* 3, 1501-5 (1997).
16. Bhargava, P. et al. A Phase I and pharmacokinetic study of TNP-470 administered weekly to patients with advanced cancer. *Clin Cancer Res* 5, 1989-95 (1999).
17. Herbst, R. S. et al. Safety and pharmacokinetic effects of TNP-470, an angiogenesis inhibitor, combined with paclitaxel in patients with solid tumors: evidence for activity in non-small-cell lung cancer. *J Clin Oncol* 20, 4440-7 (2002).
18. Kim, E. S. & Herbst, R. S. Angiogenesis inhibitors in lung cancer. *Curr Oncol Rep* 4, 325-33 (2002).

19. Stadler, W. M. et al. Multi-institutional study of the angiogenesis inhibitor TNP-470 in metastatic renal carcinoma *J Clin Oncol* 17, 2541-5 (1999).
20. Logothetis, C. J. et al. Phase I trial of the angiogenesis inhibitor TNP-470 for progressive androgen-independent prostate cancer. *Clin Cancer Res* 7, 1198-203 (2001).
21. Rupnick, M. A. et al. Adipose tissue mass can be regulated through the vasculature. *Proc Natl Acad Sci USA* 99, 10730-5 (2002).
22. Schoof, D. D. et al. The influence of angiogenesis inhibitor AGM-1470 on immune system status and tumor growth in vitro. *Int J Cancer* 55, 630-5 (1993).
23. Nagabuchi, E., VanderKolk, W. E., Une, Y. & Ziegler, M. M. TNP-470 antiangiogenic therapy for advanced murine neuroblastoma. *J Pediatr Surg* 32, 287-93 (1997).
24. Rihova, B. et al. Biocompatibility of N-(2-hydroxypropyl)methacrylamide copolymers containing adriamycin. Immunogenicity, and effect on haematopoietic stem cells in bone marrow in vivo and mouse splenocytes and human peripheral blood lymphocytes in vitro. *Biomaterials* 10, 335-42. (1989).
25. Seymour, L. W., Ulbrich, K., Strohalm, J., Kopecek, J. & Duncan, R. The pharmacokinetics of polymer-bound adriamycin. *Biochem Pharmacol* 39, 1125-31 (1990).
26. Maeda, H., Wu, J., Sawa, T., Matsumura, Y. & Hori, K Tumor vascular permeability and the EPR effect in macromolecular therapeutics: a review. *J Control Release* 65, 271-84 (2000).
27. Duncan, R., Coatsworth, J. K. & Burtles, S. Preclinical toxicology of a novel polymeric antitumour agent: HPMA copolymer-doxombicin (PK1). *Hum Exp Toxicol* 17, 93-104 (1998).
28. Satchi-Fainaro, R. Targeting tumour vasculature: Reality or a dream? *J Drug Targeting* 10, 529-533 (2002).
29. Duncan, R., Cable, H. C., Lloyd, J. B., Rejmanova, P. & Kopecek, J. Polymers containing enzymatically degradable bonds, 7. Design of oligopeptide side chain in poly N-(2-hydroxypropyl)methacrylamide copolymers to promote efficient degradation by lysosomal enzymes. *Makromol Chem* 184, 1997-2008 (1984).
30. Foekens, J. A. et al. Prognostic significance of cathepsins B and L in primary human breast cancer. *J Clin Oncol* 16, 1013-21 (1998).
31. Gianasi, E. et al. HPMA copolymer platinates as novel antitumour agents: in vitro properties, pharmacokinetics and antitumour activity in vivo. *Eur J Cancer* 35, 994-1002 (1999).
32. Kusaka, M. et al. Cytostatic inhibition of endothelial cell growth by the angiogenesis inhibitor TNP-470 (AGM-1470). *Br J Cancer* 69, 212-6 (1994).
33. Greene, A. K. et al. Endothelial directed hepatic regeneration after partial hepatectomy. *Annals of Surgery* in press (2003).
34. Drixler, T. A. et al. Liver regeneration is an angiogenesis-associated phenomenon. *Ann Surg* 236, 703-12 (2002).
35. Klein, S. A., Bond, S. J., Gupta, S. C., Yacoub, O. A. & Anderson, G. L. Angiogenesis inhibitor TNP-470 inhibits murine cutaneous wound healing. *J Surg Res* 82, 268-74 (1999).
36. Whalen, C. T., Hanson, G. D., Putzer, K. J., Mayer, M. D. & Mulford, D. J. Assay of TNP-470 and its two major metabolites in human plasma by high-performance liquid chromatography-mass spectrometry. *J Chromatogr Sci* 40, 214-8 (2002).
37. Brocchini, S. & Duncan, R. Polymer-Drug conjugates: drug release from pendent linkers. in *Encyclopaedia of controlled release* (ed. Mathiovitz, E.) 786-816 (New York: Wiley, 1999).
38. Duncan, R. et al. Polymer-drug conjugates, PDEPT and PELT: basic principles for design and transfer from the laboratory to clinic. *J Control Release* 74, 135-46 (2001).
39. Vasey, P. A. et al. Phase I clinical and pharmacokinetic study of PK1 [N-(2-hydroxypropyl)methacrylamide copolymer doxorubicin]: first member of a new class of chemotherapeutic agents-drug-polymer conjugates. Cancer Research Campaign Phase I/II Committee. *Clin Cancer Res* 5, 83-94 (1999).
40. Seymour, L. W. et al. Tumour tropism and anti-cancer efficacy of polymer-based doxorubicin prodrugs in the treatment of subcutaneous murine B16F10 melanoma. *Br J Cancer* 70, 636-41 (1994).
41. Dvorak, H. F., Nagy, J. A., Dvorak, J. T. & Dvorak, A. M. Identification and characterization of the blood vessels of solid tumors that are leaky to circulating macromolecules. *Am J Pathol* 133, 95-109 (1988).
42. Griffith, E. C. et al. Methionine aminopeptidase (type 2) is the common target for angiogenesis inhibitors AGM-1470 and ovalicin. *Chem Biol* 4, 461-71 (1997).
43. Auerbach, R., Akhtar, N., Lewis, R. L. & Shinners, B. L. Angiogenesis assays: problems and pitfalls. *Cancer Metastasis Rev* 19, 167-72 (2000).
44. Seymour, L. W. et al. Hepatic drug targeting: phase I evaluation of polymer-bound doxorubicin. *J Clin Oncol* 20, 1668-76 (2002).
45. Francis, G. E., Delgado, C. & Fisher, D. PEG-modified proteins. in *Stability of proteins pharmaceuticals (Part B)* (ed. Ahem T J, M. M.) 235-263 (Plenum Press, New York, 1992).
46. Ho, D. H. et al. Clinical pharmacology of polyethylene glycol-L-asparaginase. *Drug Metab Dispos* 14, 349-52 (1986).
47. O'Reilly, M. S. et al. Angiostatin: a novel angiogenesis inhibitor that mediates the suppression of metastases by a Lewis lung carcinoma. *Cell* 79, 315-28 (1994).
48. Folkman, J., Haudenschild, C. C. & Zetter, B. R. Long-term culture of capillary endothelial cells. *Proc Natl Acad Sci USA* 76, 5217-21 (1979).
49. Paxinos, J. & Franklin, K. B. J. *The Mouse Brain in Stereotaxic Coordinates*, (Academic Press, 2001).
50. Waynforth, H. B. Routes and methods of administration, Intracerebral injection. in *Experimental and Surgical technique in the rat*, Vol. 2.9 34-36 (Academic Press, London, 1980).

Although the foregoing invention has been described in some detail by way of illustration and example for the purposes of clarity of understanding, one skilled in the art will easily ascertain that certain changes and modifications may be practiced without departing from the spirit and scope of the appended claims.

What is claimed is:

1. A composition comprising a TNP-470 conjugated to a polymer, wherien the polymer is water soluble and has a molecular weight not greater than 60 kDa, wherein the polymer is a hydroxypropyl(meth)acrylamide-methacrylic acid copolymer.

2. The composition of claim 1, wherein the polymer has a molecular weight in the range of 15 to 40 kDa.

3. The composition of claim 1, futher comprising a peptide linker between the TNP-470 and the polymer.

4. The composition of claim 1, further comprising a targeting ligand.

5. The composition of claim 1, comprising the structure:

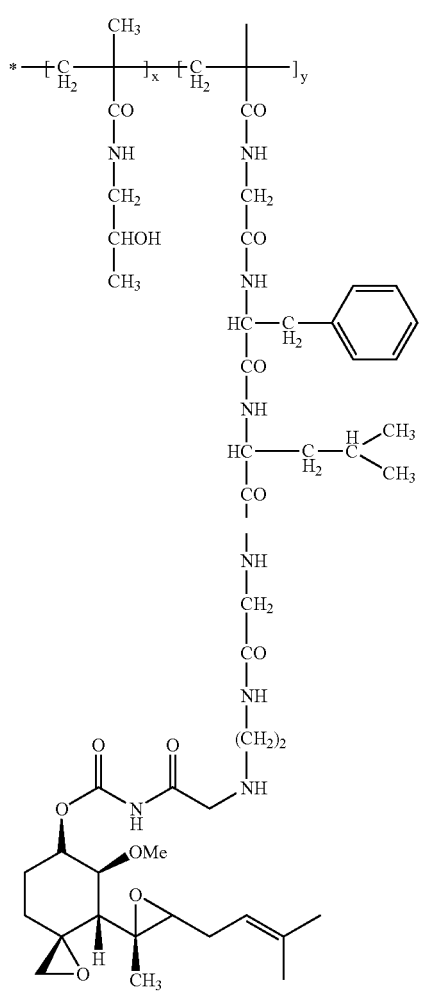

wherein y is in the range of 0.04-20 and x is in the range of 80-99.96.

6. A method of treating an angiogenic disease comprising administering a composition of claim 1 to a mammal in need thereof, wherein the angiogenic disease is a solid tumor, a lymphoma, a leukemia, diabetic retinopathy or macular degeneration.

7. A method for decreasing neurotoxicity of TNP-470, comprising conjugating the TNP-470 to a polymer, wherein the polymer is water soluble and has a molecular weight not greater than 60 kDa.

8. The nethod of claim 7, wherein the polymer has a molecular weight in the range of 15 to 40 kDa.

9. The method of claim 7, wherein the polymer is a hydroxypropyl(meth)acrylamide-methacrylic acid copolymer.

10. The method of claim 7, further comprising a peptide linker between the antiangiogenic agent and the polymer.

11. The method of claim 7, comprising the structure:

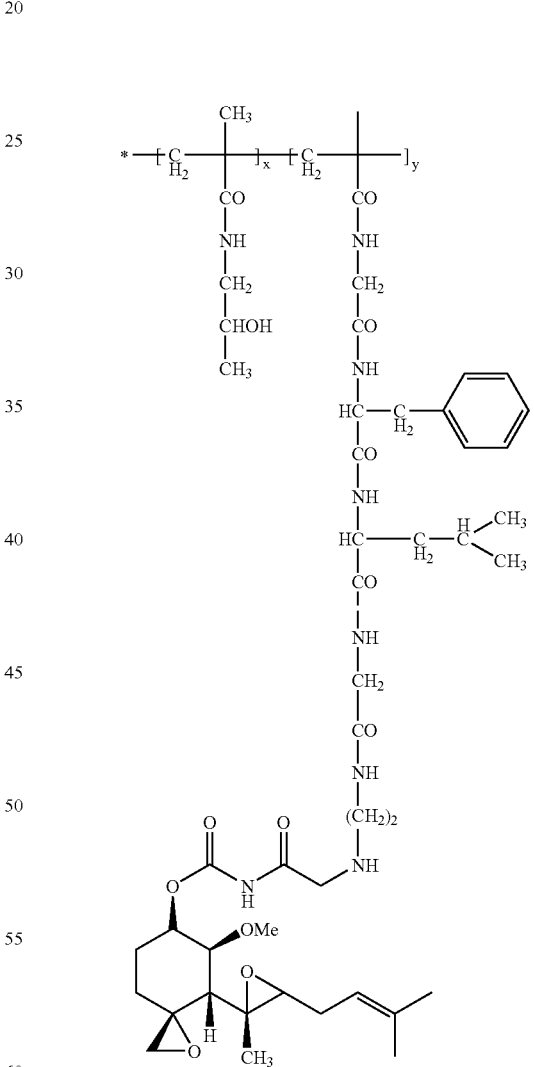

wherein y is in the range of 0.04-20 and x is in the range of 80-99.96.

12. The method of claim 11, wherein y is 5-10 and x is 90-95.
13. An HPMA-TNP-470 conjugate comprising the structure:
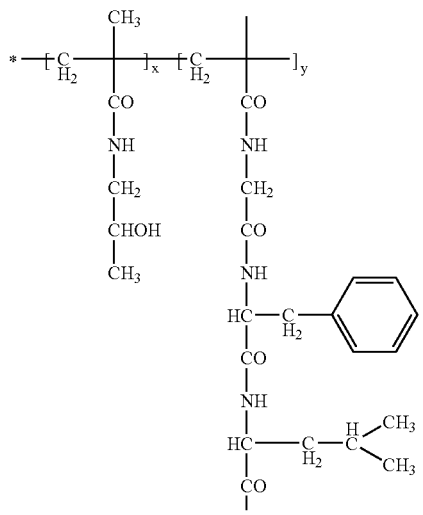
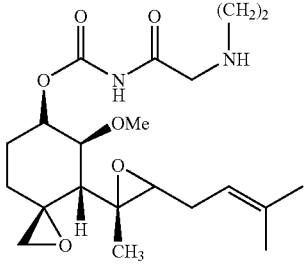
wherein x is 90-95 and y is 5-10.
* * * * *